(12) United States Patent
Knight

(10) Patent No.: US 7,763,467 B2
(45) Date of Patent: Jul. 27, 2010

(54) DRIP SHIELD

(75) Inventor: Byron J. Knight, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 806 days.

(21) Appl. No.: 11/673,903

(22) Filed: Feb. 12, 2007

(65) Prior Publication Data

US 2007/0189924 A1 Aug. 16, 2007

Related U.S. Application Data

(60) Provisional application No. 60/772,575, filed on Feb. 13, 2006.

(51) Int. Cl.
*G01N 35/10* (2006.01)
*G01N 1/02* (2006.01)

(52) U.S. Cl. .............. 436/49; 436/43; 436/45; 436/180; 422/63; 422/64; 422/65; 422/99; 422/100

(58) Field of Classification Search .................. None
See application file for complete search history.

(56) References Cited

U.S. PATENT DOCUMENTS

| | | | |
|---|---|---|---|
| 4,276,258 A * | 6/1981 | Ginsberg et al. | 422/64 |
| 5,084,242 A | 1/1992 | Sakuma et al. | |
| 5,510,082 A * | 4/1996 | Arai et al. | 422/64 |
| 6,335,166 B1 | 1/2002 | Ammann et al. | |
| 2007/0110626 A1 * | 5/2007 | Baumann et al. | 422/99 |
| 2007/0128085 A1 * | 6/2007 | Burkhardt et al. | 422/102 |
| 2008/0063567 A1 * | 3/2008 | Schacher et al. | 422/68.1 |

FOREIGN PATENT DOCUMENTS

| | | |
|---|---|---|
| EP | 410 645 A2 * | 7/1990 |
| WO | WO 03/008099 A2 | 1/2003 |
| WO | WO 03/097240 A2 | 11/2003 |

OTHER PUBLICATIONS

International Search Report for PCT/US2007/003824 filed Feb. 12, 2007, 3 pages, (Aug. 16, 2007).
Written Opinion of the International Searching Authority for PCT/US2007/003824 filed Feb. 12, 2007, 7 pages (Aug. 16, 2007).
PCT International Preliminary Report on Patentability, International Application No. PCT/US07/003824, Aug. 28, 2008.

* cited by examiner

*Primary Examiner*—P. Kathryn Wright
(74) *Attorney, Agent, or Firm*—Rothwell, Figg, Ernst & Manbeck, PC; Charles B. Cappellari, Esq.

(57) ABSTRACT

A drip shield includes cover members that define a protective canopy over sample receptacles to prevent unwanted material from being deposited into the receptacles. The cover members cooperate to define at least one access hole through the drip shield to permit access to a sample receptacle by a pipette tip through the access hole. One of the cover members is moveable with respect to another cover member between a closed stated defining the access hole and an open state permitting a pipette tip extending through the access hole to be laterally conveyed relative to the drip shield and out of the access hole. In a preferred embodiment, a system control feature automatically determines if a pipette tip might have been left in a sample receptacle and extending through the access hole of the drip shield and thereby cause the sample receptacle and pipette tip to be conveyed laterally relative to the drip shield while the one cover member moves from the closed to the open state to permit the pipette tip to be conveyed out of the access hole.

31 Claims, 16 Drawing Sheets

DRIP SHIELD

This application claims the benefit of U.S. Provisional Application No. 60/772,575, filed Feb. 13, 2006, the disclosure of which is incorporated by reference.

FIELD OF THE INVENTION

The present invention relates to a drip shield for protecting against cross-contamination between sample tubes and is especially suited for use with an automated sampling system and sample tubes having penetrable caps. The drip shield permits a sample tube to be conveyed laterally beneath the drip shield even when a disposable pipette tip becomes dislodged from an automated sampling device and extends up from the sample tube through an access hole in the drip shield.

BACKGROUND OF THE INVENTION

Procedures for determining the presence or absence of specific organisms or viruses in a test sample commonly rely upon nucleic acid-based probe testing. To increase the sensitivity of these tests, an amplification step is often included to increase the number of potential nucleic acid target sequences present in the test sample. There are many amplification procedures in common use today, including the polymerase chain reaction (PCR), Q-beta replicase, self-sustained sequence replication (3SR), transcription-mediated amplification (TMA), nucleic acid sequence-based amplification (NASBA), ligase chain reaction (LCR), strand displacement amplification (SDA) and loop-mediated isothermal amplification (LAMP), each of which is well known in the art. See, e.g., Mullis, "Process for Amplifying Nucleic Acid Sequences," U.S. Pat. No. 4,683,202; Erlich et al., "Kits for Amplifying and Detecting Nucleic Acid Sequences," U.S. Pat. No. 6,197,563; Walker et al., *Nucleic Acids Res.*, 20:1691-1696 (1992); Fahy et al., "Self-sustained Sequence Replication (3SR): An Isothermal Transcription-Based Amplification System Alternative to PCR," *PCR Methods and Applications*, 1:25-33 (1991); Kacian et al., "Nucleic Acid Sequence Amplification Methods," U.S. Pat. No. 5,399,491; Davey et al., "Nucleic Acid Amplification Process," U.S. Pat. No. 5,554,517; Birkenmeyer et al., "Amplification of Target Nucleic Acids Using Gap Filling Ligase Chain Reaction," U.S. Pat. No. 5,427,930; Marshall et al., "Amplification of RNA Sequences Using the Ligase Chain Reaction," U.S. Pat. No. 5,686,272; Walker, "Strand Displacement Amplification," U.S. Pat. No. 5,712,124; Notomi et al., "Process for Synthesizing Nucleic Acid," U.S. Pat. No. 6,410,278; Dattagupta et al., "Isothermal Strand Displacement Amplification," U.S. Pat. No. 6,214,587; and HELEN H. LEE ET AL., NUCLEIC ACID AMPLIFICATION TECHNOLOGIES: APPLICATION TO DISEASE DIAGNOSIS (1997).

A concern with amplification is the possibility of cross-contamination, since transferring even a minute amount of target-containing sample to a target-negative sample could lead to the production of billions of target sequences in the "negative" sample. As a consequence, a test may indicate a positive result for a sample actually lacking nucleic acid from an organism or virus of interest. The source of a contaminating sample transfer may be an aerosol or bubbles released from a sample tube when a cap component of the sample tube is removed or penetrated by a practitioner or instrument. To minimize such sources of contamination, collection devices which include penetrable caps having filtering means have been introduced for use with automated analyzers. Such collection devices include the APTIMA® Urine Specimen Collection Kit for Male and Female Urine Specimens (Gen-Probe Incorporated, San Diego, Calif.; Cat. No. 1040), which is an embodiment of the collection devices disclosed by Kacian et al., "Penetrable Cap," U.S. Pat. No. 6,893,612.

The components of a penetrable cap generally exert a retention force against a fluid transfer device (e.g., pipette tip) as the fluid transfer device is being withdrawn from an associated sample tube. See, e.g., Ammann et al., "Automated Process for Isolating and Amplifying a Target Nucleic Acid Sequence," U.S. Pat. No. 6,335,166 (an instrument for performing amplification assays on test samples which includes a robotic pipettor using disposable pipette tips for obtaining test sample from a sample tube is disclosed). The retention force may be attributable to, for example, the sealing material of the cap and/or filtering means included within the cap exerting a frictional force on the fluid transfer device. The retention force may also be caused by a swab used for specimen collection (e.g., a cervical, urethral or urinary tract specimen) which is angled in the sample tube or where multiple swabs have been inadvertently inserted into the same sample tube. Swabs used for specimen collection may be provided with a mid-section score line for snapping off the upper portion of the swab. (Such swabs are described by Pestes et al., "Cell Collection Swab," U.S. Pat. No. 5,623,942, and one such commercial product is the APTIMA® Unisex Swab Specimen Collection Kit for Endocervical and Male Urethral Swab Specimens, available from Gen-Probe as Cat. No. 1041.) If properly broken, the remainder of the swab should fit along the inner wall of the sample tube below the cap. But, if the snap occurs above the score line, then when the swab is fitted into the sample tube, and the cap is screwed onto the sample tube, the swab may bow in such a way that it interferes with the path of a pipette tip inserted through the cap.

If the retention force is too great, attempts to remove the fluid transfer device from the associated sample tube could result in the sample tube being withdrawn from a sample carrier holding the sample tube. In a more extreme case, the retention force of the cap and the sample tube holding force of the sample carrier are each great enough that the sample carrier is lifted vertically as the fluid transfer device is being withdrawn from the sample tube.

Conventional sample carriers commonly rely upon springs to immobilize sample tubes, biasing the sample tubes against one or more opposing surfaces of the sample carriers. And more recently, a sample carrier has been described which further includes a top wall portion having a plurality of openings which are configured and arranged so that penetrable caps affixed to the vessel components of sample tubes are positioned snugly within the openings when the sample tubes are held by the sample carrier, thereby centering the sample tubes by restricting lateral movement of the corresponding caps within the openings. See Sevigny et al., "Sample Carrier and Drip Shield for Use Therewith," U.S. Pat. Application Publication No. US 2003-0215365 A1. Furthermore, the sample carriers described include a mechanism, such as a sample tube blocking member, for ensuring that sample tubes remain in the sample carriers during automated sampling procedures when the retention force generated by a cap onto a portion of the fluid transfer device (e.g., pipette tips) is greater than the holding force of the sample carrier on an associated sample tube component.

Furthermore, a drip shield has been described for use in an automated sampling system to protect the contents of sample tubes held by sample carriers from fluid contamination, especially hanging droplets which may be dislodged from a robotic pipetting device during an automated sampling procedure. See Sevigny et al., "Sample Carrier and Drip Shield for Use Therewith," U.S. Patent Application Publication No. US 2003-0215365 A1. By "automated sampling system" is meant a system for holding a sample tube in a generally upright orientation and conveying the sample tube by automated means (e.g., a transport mechanism) to a location within an apparatus where the contents of the sample tube may be accessed by an automated substance transfer mechanism, such as a robotic pipetting device, in order to effect a transfer of at least a portion of the contents to another location within the apparatus. The drip shield includes a cover member having one or more access holes, where each access hole is configured and arranged to provide non-interfering, vertical passage of an aligned pipette tip therethrough. The access holes are sized to permit access to the contents of only one sample tube at a time, where the sample tubes being accessed are present in a sample carrier positioned beneath the cover member. The diameter of each access hole is preferably the same as or smaller than the smallest diameter of any sample tube cap associated with a sample tube held by the sample carrier to minimize opportunities for contaminating the sample carrier and its contents.

A potential problem associated with the above-described sample carrier and drip shield configurations occurs when a disposable pipette tip is dislodged from a pipette tip mounting shaft of a robotic pipetting device while the pipette tip is inserted through an access hole in the drip shield and into the sample tube. The pipette tip can, for example, become unseated or dislodged when the frictional retention force created by the sample tube cap or a specimen collection swab (as described above) on the pipette tip, as the pipette tip is being withdrawn from the cap, exceeds the force required to dislodge the pipette tip from the pipette tip mounting shaft. When a pipette tip becomes dislodged and extends upward through an access hole of the drip shield, the sample carrier is prevented from advancing beneath the drip shield. To correct this problem, an operator must terminate operation of the apparatus, reach into the apparatus and remove the dislodged pipette tip or push the pipette tip far enough into the sample tube to clear the drip shield. This corrective procedure can be awkward and inconvenient—if not altogether impossible—if the sample transfer location is in a difficult to access location within the apparatus. Ideally, sample carriers could be conveyed away from the drip shield on a lateral transport path to a location where the operator could more easily reach and remove the dislodged pipette tip.

Accordingly, a need exists for a drip shield design that will allow the sample carrier to be conveyed laterally away from the drip shield when a dislodged pipette tip extends through an access hole of the drip shield, while still maintaining protection of the sample tubes being conveyed beneath the drip shield.

SUMMARY

Aspects of the invention are embodied in an apparatus for preventing unwanted materials from being deposited into receptacles carried by an automated conveyor. In one embodiment, the apparatus includes a first cover member and a second cover member configured to be moveable with respect to the first cover member between a closed state and an open state. In the closed state, the second cover member is operatively positioned with respect to the first cover member so that the first and second cover members cooperate to define one or more access holes for receiving pipette tips therethrough to access receptacles positioned beneath the apparatus. In the open state, the second cover member is operatively positioned with respect to the first cover member so that at least one of the access holes is laterally opened, thereby permitting a pipette tip extending through the access hole to be laterally conveyed relative to the apparatus and away from the location of the access hole. Thus, when a pipette tip disengages from a substance transfer mechanism, remaining within a receptacle and extending up through the access hole, an associated transport mechanism is able to move the receptacle to a location within the instrument at which a technician can access and remove the pipette tip.

In one embodiment, the first cover member includes one or more slots extending from an end portion thereof, and the second cover member includes a cover portion which, when in the closed state, covers all but a portion of the one or more slots, the uncovered portion of the slots composing the access holes. The cover portion of the second cover member may have an edge, for example an undulating edge, that is engaged by a pipette tip extending through one of the access holes as the pipette tip is conveyed laterally, thereby causing the second cover member to move relative to the first cover member from the closed state to the open state.

Other aspects of the invention are embodied in a system for transferring substance to or from each of a plurality of receptacles. The system includes a substance transfer mechanism, a transport mechanism, and a drip shield. The substance transfer mechanism is used in conjunction with a pipette tip and is adapted to insert a pipette tip removably engaged by the substance transfer mechanism into a receptacle to transfer substance to or from the receptacle. The transport mechanism is adapted to move a plurality of receptacles in generally upright orientations into an operative location with respect to the substance transfer mechanism, where the substance transfer mechanism can access each receptacle to insert a pipette tip into the receptacle. The drip shield is disposed over a portion of the transport mechanism at the operative location for preventing unwanted materials from being deposited into receptacles carried by the transport mechanism. In one embodiment, the drip shield includes a first cover member and a second cover member configured to be moveable with respect to the first cover member between a closed state and an open state. In the closed state, the second cover member is operatively positioned with respect to the first cover member so that the first and second cover members cooperate to define one or more access holes for receiving a pipette tip therethrough to access a receptacle positioned beneath the drip shield. And in the open state, the second cover member is operatively positioned with respect to the first cover member so that at least one of the access holes is laterally opened, thereby permitting a pipette tip extending through the access hole to be laterally conveyed by the transport mechanism relative to the drip shield and away from the location of the access hole.

Still further aspects of the invention are embodied in a method for transferring substance to or from a receptacle and for preventing unwanted materials from being deposited into the receptacle comprising. The method includes providing, at a substance transfer location, an apparatus, such as described above, for preventing unwanted materials from being deposited into receptacles carried by an automated conveyor. The method further includes transporting a receptacle to the substance transfer location; accessing the receptacle through one of the access holes of the apparatus with a pipette tip engaged by a substance transfer mechanism; and transferring substance into or out of the pipette tip accessing the receptacle through the access hole. After the transferring step, if the pipette tip is no longer engaged by the substance transfer mechanism, the receptacle is conveyed laterally with respect to the apparatus. If the pipette tip no longer engaged by the substance transfer mechanism is extending through the access hole, the second cover member is caused to move from the closed state to the open state to permit the pipette tip extending through the access hole to be laterally conveyed by the transport mechanism relative to the apparatus and away from the location of the access hole.

Other objects, features, and characteristics of the present invention, including the methods of operation and the function and interrelation of the elements of structure, will become more apparent upon consideration of the following description and the appended claims, with reference to the accompanying drawings, all of which form a part of this disclosure, wherein like reference numerals designate corresponding parts in the various figures.

DETAILED DESCRIPTION

While the present invention may be embodied in a variety of forms, the following description and accompanying drawings are merely intended to disclose some of those forms as specific examples of the present invention. Accordingly, the present invention is not intended to be limited to the forms or embodiments so described and illustrated. Instead, the full scope of the present invention is set forth in the appended claims.

Figure 1:
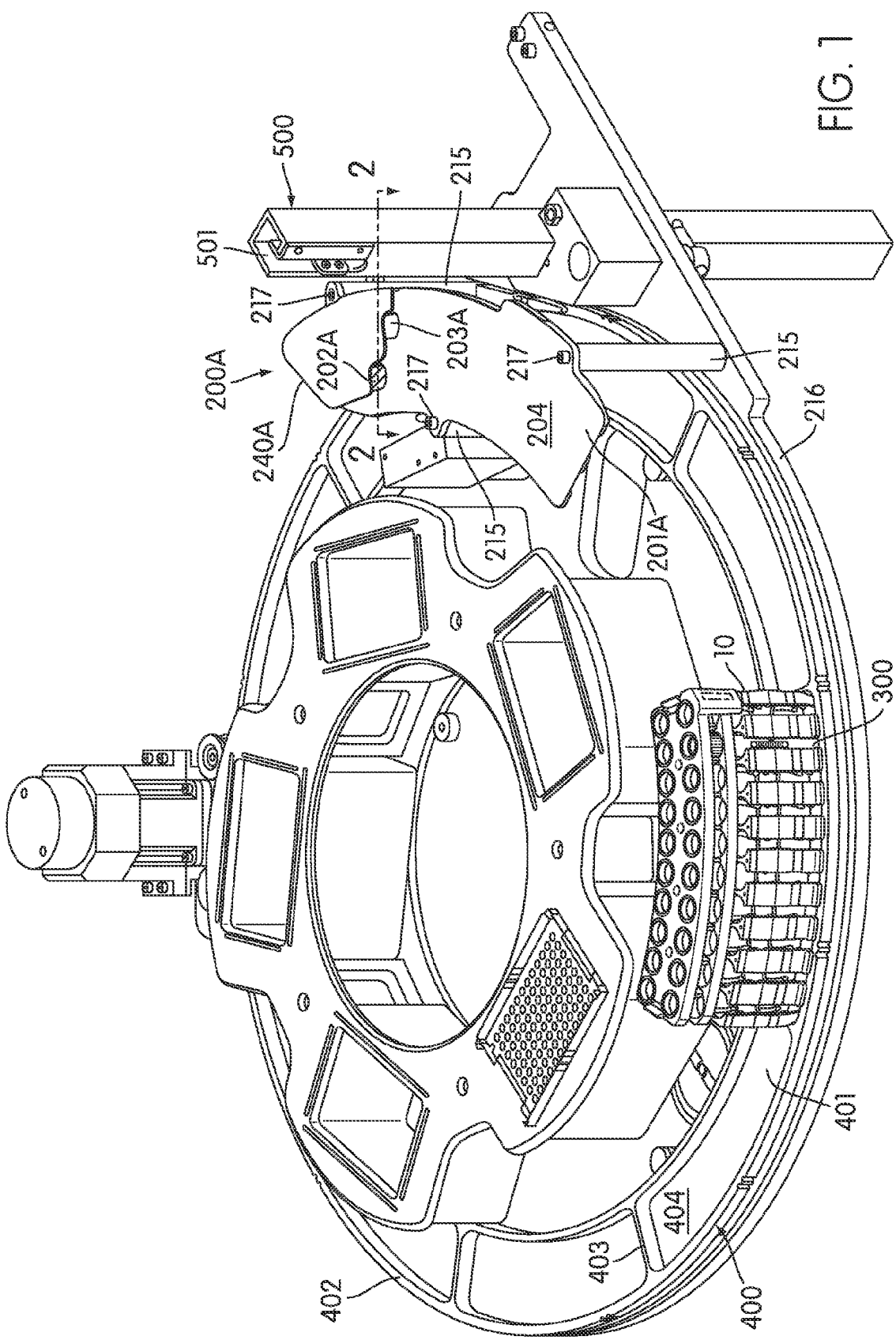
FIG. 1 is a perspective view showing a drip shield according to a first embodiment of the invention positioned above a sample transport carousel holding a sample carrier.

As shown in FIG. 1, a sample carrier 10 is provided to carry a plurality of receptacles, such as sample tubes 300, and may be adapted for use with a sample carrier conveying means, such as a sample carousel for rotating a plurality of sample carriers within an automated sampling system. One such sample carousel 400 is disclosed by Ammann et al. in U.S. Pat. No. 6,335,166 and is illustrated in FIG. 1. This particular sample carousel 400 is formed of milled, unhardened aluminum and includes an annular trough 401 about the periphery of a ring 402 and a plurality of raised, radially extending dividers 403. The dividers 403 divide the trough 401 into nine arcuate sample carrier receiving wells 404 which can be configured to accommodate the sample carriers 10. The individual sample carrier receiving wells 404 are dimensioned to maintain the sample carriers 10 in an upright position as sample tubes 300 held by the sample carriers 10 are indexed under a substance transfer mechanism, such as a robotic pipettor (not shown), for retrieving sample material for analysis. An example of a robotic pipettor for use with the present invention is the Robotic Sample Processor, Model No. RSP 9000, available from Cavro Scientific Instruments, Inc. of Sunnyvale, Calif.

Those of ordinary skill in the art will appreciate that, as an alternative to the carousel 400 shown in FIG. 1, a sample carrier conveying means may comprise a linear transport conveyor or a transport conveyor of some other configuration.

The sample carriers 10 can be used in combination with a device for protecting sample tubes 300 during sampling to limit opportunities for cross-contamination. Such a device is provided by a novel drip shield 200 depicted in FIGS. 1-19 for preventing unwanted materials from being deposited into the sample tubes 300. (Reference herein to "drip shield 200" is a general reference to any of the illustrated drip shields 200A-C.) Drip shield 200A shown in FIG. 1 is an assembly which includes a first cover member, for example in the form of a cover plate 201A, and a second cover member, for example in the form of a shutter 240A, which are dimensioned and cooperate to form a canopy over a sample carrier 10 positioned thereunder. (Reference herein to "cover plate 201" and to "shutter 240" are general references to any of the illustrated cover plates 201A-C and shutters 240A-C, respectively.) Thus, in the illustrated embodiment, the drip shield 200 has an arcuate shape corresponding to the preferred arcuate shape of the sample carrier 10, as shown in FIG. 1. That is, the general shape and configuration of the drip shield can be selected to conform to the shape and configuration of the sample carrier and associated conveying means. For example, a drip shield implemented in combination with a linear conveying means would have a linear shape.

Figure 2:
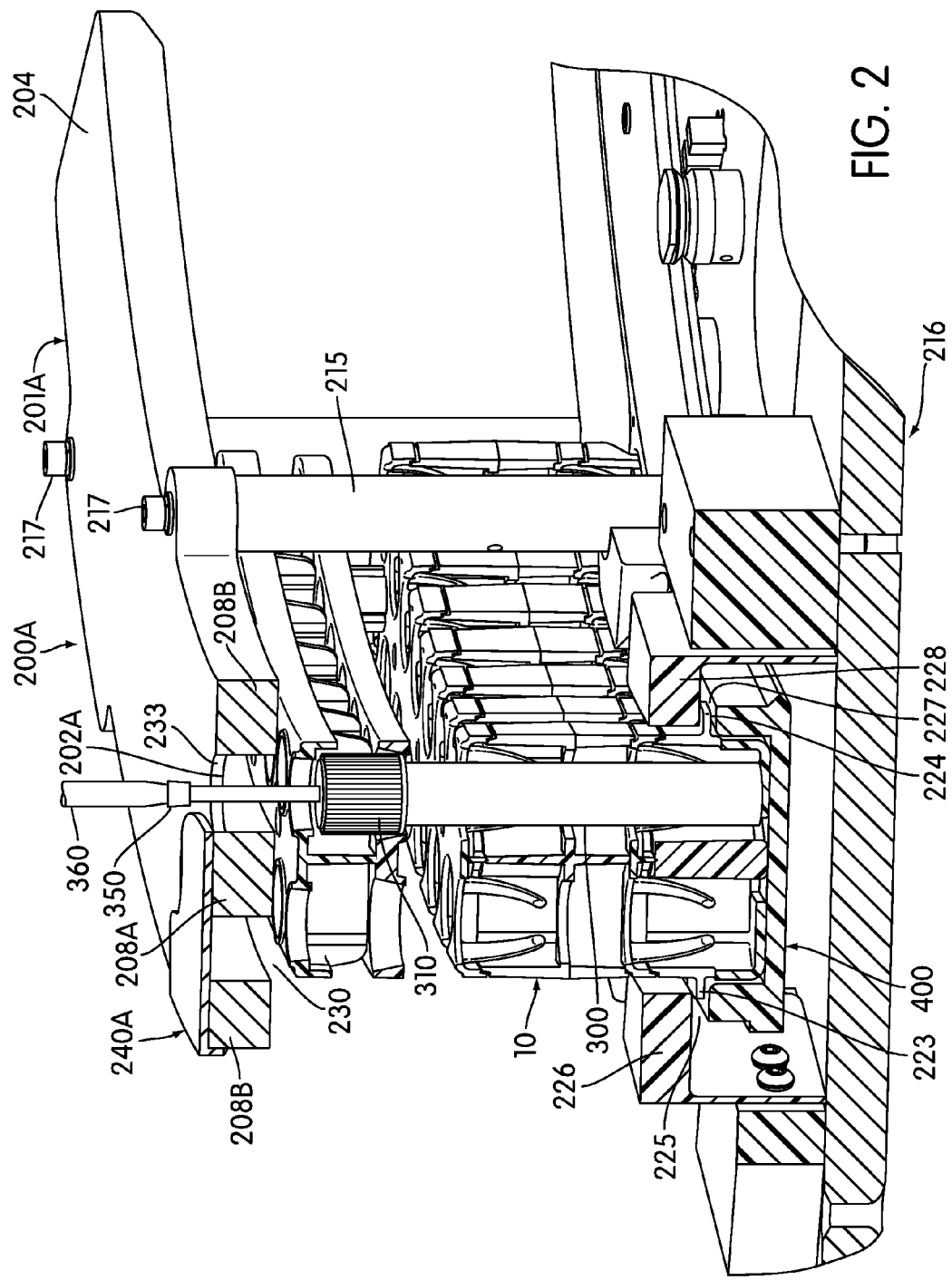
FIG. 2 is a cross-section of a portion of the drip shield, transport carousel, and sample carrier taken in the direction 2-2 in FIG. 1.

Two access holes, identified in FIG. 1 as a first, or inner, access hole 202A and a second, or outer, access hole 203A, extend through the drip shield 200 and provide access to sample tubes 300 centered below the access holes. (Reference herein to "access hole 202" or "access hole 203" is a general reference to any of the illustrated access holes 202A-C and 203A-C.) The access holes 202, 203 are dimensioned to permit non-interfering passage therethrough by pipette tips carried by a robotic pipettor, but are small enough so that a top surface 204 of the drip shield 200 can function to catch hanging droplets which are dislodged from the pipette tips during sample transfer procedures. Therefore, the diameters of the first and second access holes 202, 203, respectively, are preferably about the same as or less than the smallest diameter of any cap 310 of a sample tube 300 to be carried by a sample carrier 10, as shown in FIG. 2.

Cap 310 may be a penetrable closure device having one or more frangible seals and, optionally, a filter means (e.g., as described in Kacian, et al., U.S. Pat. No. 6,893,612) which are pierceable by the pipette tip. Other closure devices that can be pierced by a pipette include those disclosed by Anderson et al., "Penetrable Cap," U.S. Pat. No. 6,716,396. The sample tubes 300 may also contain a specimen retrieval device configured to enable a practitioner to collect an amount of specimen material and deposit the material, along with the specimen retrieval device, into a sample tube 300. An exemplary specimen retrieval device is the cell collection swab described in Pestes, et al., U.S. Pat. No. 5,623,942.

The access holes 202, 203 are arranged on the drip shield 200 so that the first access hole 202 is positioned above a first or inner row of longitudinally or arcuately aligned sample tubes 300 and the second access hole 203 is aligned above a second or outer row of longitudinally or arcuately aligned sample tubes 300. As the sample carrier 10 is indexed clockwise or counterclockwise under the drip shield 200 by the sample carousel 400, the next sample tube 300 in each row of tubes can be presented under one of the access holes 202, 203 for access by a robotic pipettor. The access holes 202, 203 are preferably angularly offset on the drip shield 200 to further minimize opportunities for contamination resulting from released hanging droplets of sample material. In a preferred mode, the access holes 202, 203 are arranged on the drip shield 200, as shown in FIG. 1, so that the third sample tube in the second or outer row of aligned tubes is positioned beneath the second access hole 203 as the first sample tube in the first or inner row of aligned tubes is positioned beneath the first access hole 202 when the sample carrier 10 is conveyed in a counterclockwise direction.

Figure 4:
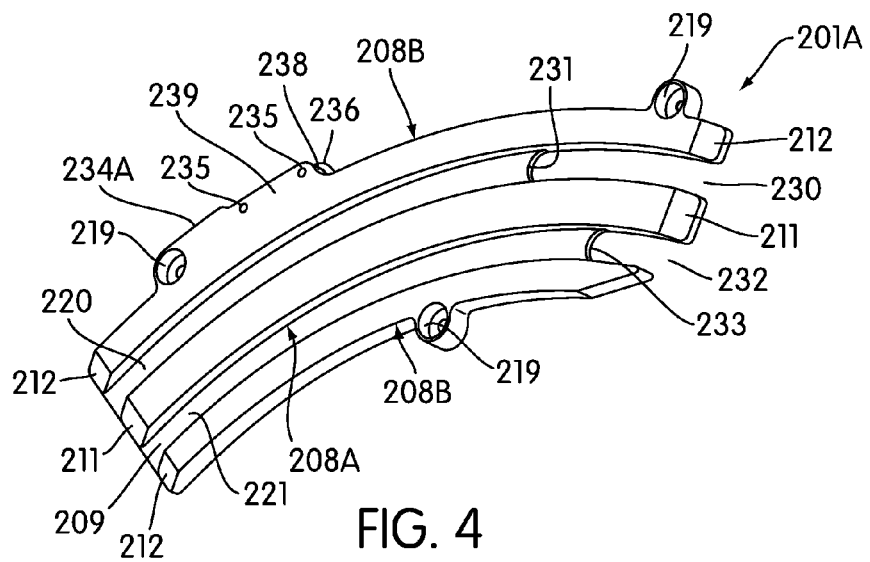
FIG. 4 is a bottom perspective view of the cover plate shown in FIG. 3.

The shutter 240 is disposed over a portion of the cover plate 201, and at least a portion of the shutter 240 is movable relative to the cover plate 201. As shown in FIG. 4, the cover plate 201A may include a series of three longitudinally or arcuately extending runners 208 which are spaced apart from each other and depend from a bottom surface 209 of the cover plate 201A so as to define a first channel 220 and a second channel 221. (The reference number "208" refers generally to all three runners shown in the figures, whereas the reference number "208A" refers to the center runner and the reference number "208B" refers to the two edge runners.) Channels 220 and 221 provide clearance under the drip shield 200 to accommodate taller sample tubes (possibly taller sample tubes without caps). The runners 208A, 208B preferably include tapered ends 211, 212, respectively, as shown in FIG. 4. The tapered ends 211, 212 of the runners 208A, 208B are provided to facilitate proper seating of sample carriers 10 which have not been fully inserted into sample carousel receiving wells 404 prior to rotation, whether the sample carousel 400 is being rotated clockwise or counterclockwise.

It should be understood that the runners 208 and channels 220, 221 are optional and are not required for the effective operation of the invention.

The sample carrier 10 shown in FIGS. 1 and 2 includes tabs 223, 224 (see FIG. 2) extending laterally from a lower end of the carrier 10. The sample carrier shown is described in Knight et al., "Sample Tube Holder," U.S. Pat. Application Publication No. US 2006-0266719 A1. Other exemplary sample carriers are described in: Dale et al., "Sample Carrier and Drip Shield for Use Therewith," U.S. Patent Application Publication No. US 2003-0017084 A1; Sevigny et al., "Sample Carrier Having Sample Tube Blocking Means and Drip Shield for Use Therewith," U.S. Patent Application Publication No. US 2003-0215365 A1; and Aviles et al., "Sample Carrier Having Releasable Locking Mechanism," U.S. Pat. No. 7,132,082. When the sample carrier 10 is in a sample transfer location (i.e., under the drip shield 200A) tabs 223 and 224 engage blocking elements which prevent the sample carrier 10 from being lifted out of the receiving well 404 of the sample carousel 400. More specifically, tab 223 extends into a gap 225 defined between the top of the sample carousel 400 and the bottom of a block element 226 mounted in a fixed position with respect to a stationary surface 216. Similarly, tab 224 extends into a gap 227 defined between the top of the sample carousel 400 and the bottom of block element 228 mounted in a fixed position with respect to the stationary surface 216. Thus, tabs 223 and 224 prevent the carrier from being lifted out of the receiving well 404.

Preferably, the distance between the bottom of the drip shield 200 and the top of a sample tube cap 310 is about 0.36 inches (9.14 mm).

Figure 3:
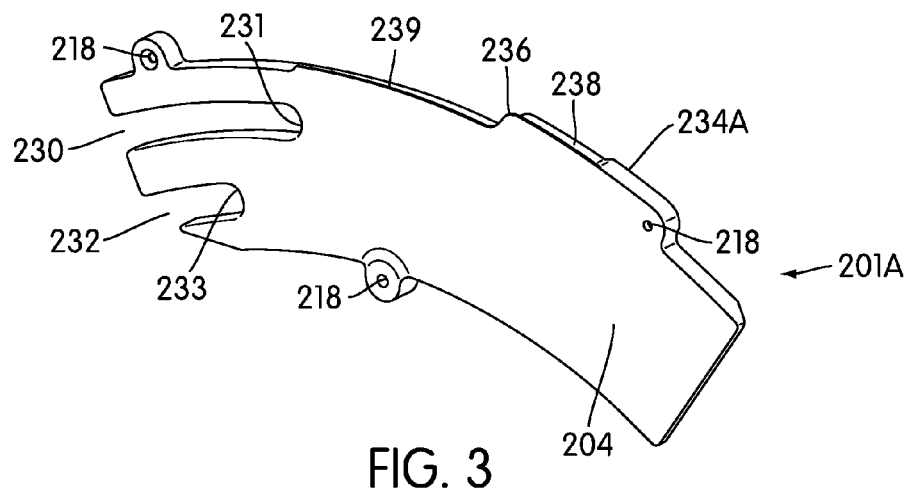
FIG. 3 is a top perspective view of a cover plate of a drip shield according to the first embodiment of the invention.

The drip shield 200 can be maintained in fixed relationship over sample carriers 10 being indexed on the sample carousel 400 therebelow by means of mounting posts 215 fixed to the stationary surface 216 of the automated sampling system, as illustrated in FIGS. 1 and 2 and more fully described by Ammann et al. in U.S. Pat. No. 6,335,166. The drip shield 200 can be secured to these mounting posts 215 using screws, bolts or like mechanical fasteners. Preferred are screws 217 mated with threaded holes (not shown) in the mounting posts 215 and inserted through three counter-bored through-holes 218 located on the periphery of the cover plate 201A, as shown in FIG. 3. The holes 218 may be countersunk in the top surface 204 of the cover plate 201A. This is especially necessary with respect to the screw 217 that is adjacent to the shutter 240A so that the screw head does not interfere with movement of the shutter 240A relative to the cover plate 201A. Cover plate 201A also includes three bored openings 219 aligned with the through-holes 218 (see FIG. 4) which receive the top ends of the mounting posts 215.

Components of the drip shield 200 of the present invention are preferably made of a substantially non-conductive plastic, such as acrylonitrile-butadiene-styrene (ABS), which can be obtained from GE Plastics of Pittsfield, Mass. as Cycolac® MG47. The materials used should be selected to resist corrosion by chemicals and reagents that the sample carrier 10 and drip shield 200 may be exposed to during use. ABS is readily available, durable and easily machined.

Referring to FIGS. 3 and 4, the cover plate 201A includes an outer slot 230 and an inner slot 232 that is somewhat shorter in length than the outer slot 230. Slots 230 and 232 are preferably arcuate in shape having a curvature generally corresponding to the curvature of the arrangement of sample tubes 300 in a sample carrier 10, which is also the curvature of the path of movement of a sample tube 300 on the sample carousel 400. Outer slot 230 has a rounded closed end 231, and inner slot 232 has a rounded closed end 233, both ends 231, 233 being located in a portion of the cover plate 201A that is interior to the outer perimeter of the cover plate. The slots 230, 232 extend from their respective ends 231, 233 to open ends at a peripheral edge of the cover plate 201A.

A shutter bracket 234A projects outwardly from an edge of the cover plate 201A and is provided for attaching the shutter 240A thereto. The shutter bracket 234A includes mounting holes 235 and perimeter ledge 236 which extends beyond a side wall 238 of the shutter bracket 234A.

Figure 5:
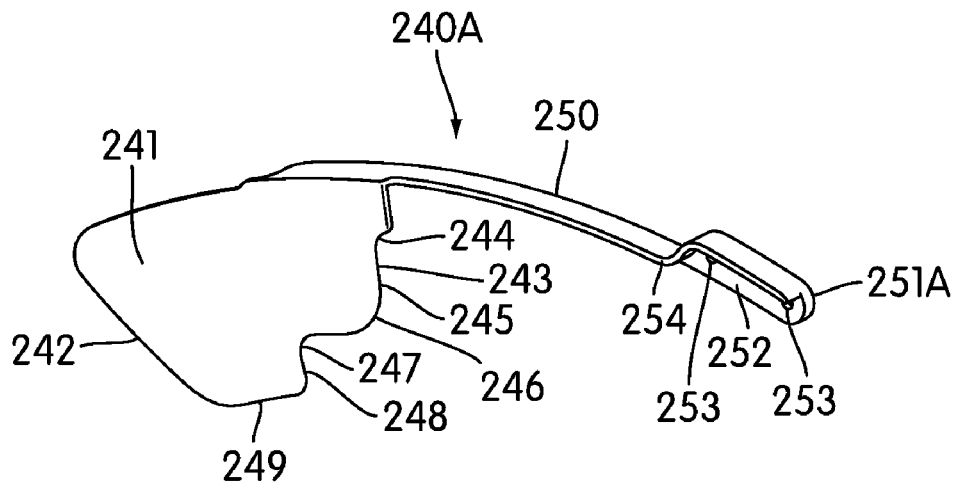
FIG. 5 is a top perspective view of a shutter of a drip shield according to the first embodiment of the invention.
Figure 6:
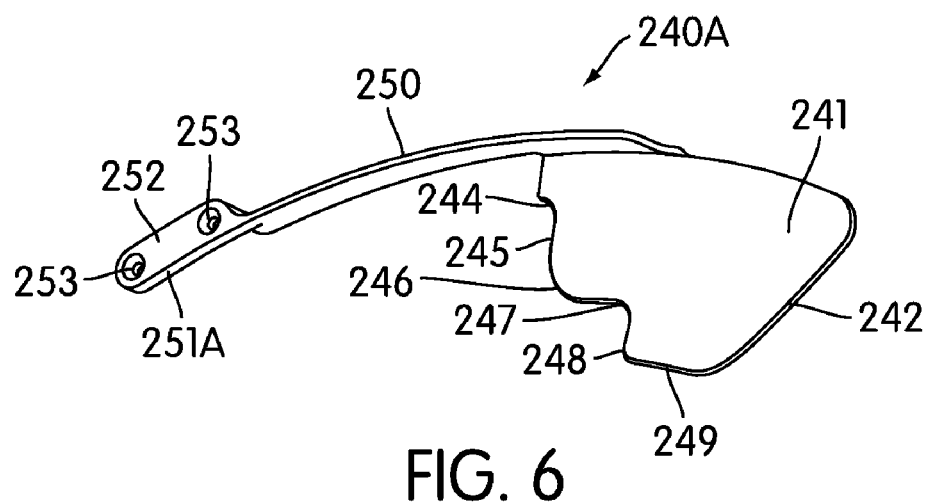
FIG. 6 is a bottom perspective view of the shutter shown in FIG. 5.

Referring to FIGS. 5 and 6, the shutter 240A includes a cover portion 241 with a flexible arm 250 and a mounting bracket 251A. The cover portion includes a sloped end 242, a inner edge 249 and an undulating edge 243. Undulating edge 243 is generally defined by a first rounded fillet 244, a first straight portion 245, a curved transition 246, a second rounded fillet 247, and a second straight portion 248 which terminates at inner edge 249.

The flexible arm 250 is in the form of a curved flexible strap arranged transversely to the plane of the cover portion 241 and extends from a peripheral edge of the cover portion 241.

The mounting bracket 251A includes a flat portion 252 with mounting holes 253 formed therein and a raised edge 254 extending along one side of the flat portion 252 until it merges with the edge of the flexible arm 250.

The shutter 240A is installed onto the cover plate 201A by placing the cover portion 241 of the shutter 240A on the top surface 204 of the cover plate 201A and engaging the flat portion 252 of the mounting bracket 251A of the shutter 240A with the bottom surface 239 of the shutter bracket 234A of the cover plate 201A. Suitable fasteners, such as screws, rivets, or bolts, extend through the mounting holes 253 of the mounting bracket 251A into the mounting holes 235, which may be threaded, of the shutter bracket 234A. The raised edge 254 of the mounting bracket 251A preferably has a thickness corresponding to the width of the perimeter ledge 236 of the shutter bracket 234A so that the raised edge 254 will seat below the perimeter ledge 236, and the edge of the flexible arm 250 will seat below a ledge 239 extending along a portion of the cover plate 201A to present a clean, flush appearance.

The cover plate 201 and the shutter 240 of are preferably machined from ABS due to the intricacy of the various features of the respective parts. Edges of the cover plate 201 and the shutter 240 are preferably rounded or chamfered so as to remove sharp edges. This is especially important in areas where the shutter and cover plate are to move relative to each other, so as to prevent one part from getting caught on the edge of the other. Persons of ordinary skill in the art will recognize that it may be possible, especially with embodiments including fewer intricate features, to form the cover plate and/or the shutter by injection molding. Furthermore, while the embodiments of the drip shield 200 shown in the drawings comprise assemblies of two or more pieces, it is contemplated that drip shields that are functionally equivalent to those shown in the drawings may be formed as a single, integrated structure.

As best shown in FIGS. 7-11, portions of the cover plate 201A and the shutter 240A cooperate to define the inner access hole 202A and outer access hole 203A. More specifically, shutter 240A covers all but a portion of the outer slot 230 so that the first fillet 244 of the shutter 240A and the rounded end 231 of the outer slot 230 form the perimeter of the outer access hole 203A (see FIG. 11). Similarly, shutter 240A covers all but a portion of the inner slot 232 so that the second fillet 247 of the shutter 240A and the rounded end 233 of the inner slot 232 cooperate to form the perimeter of the inner access hole 202A.

Figure 7:
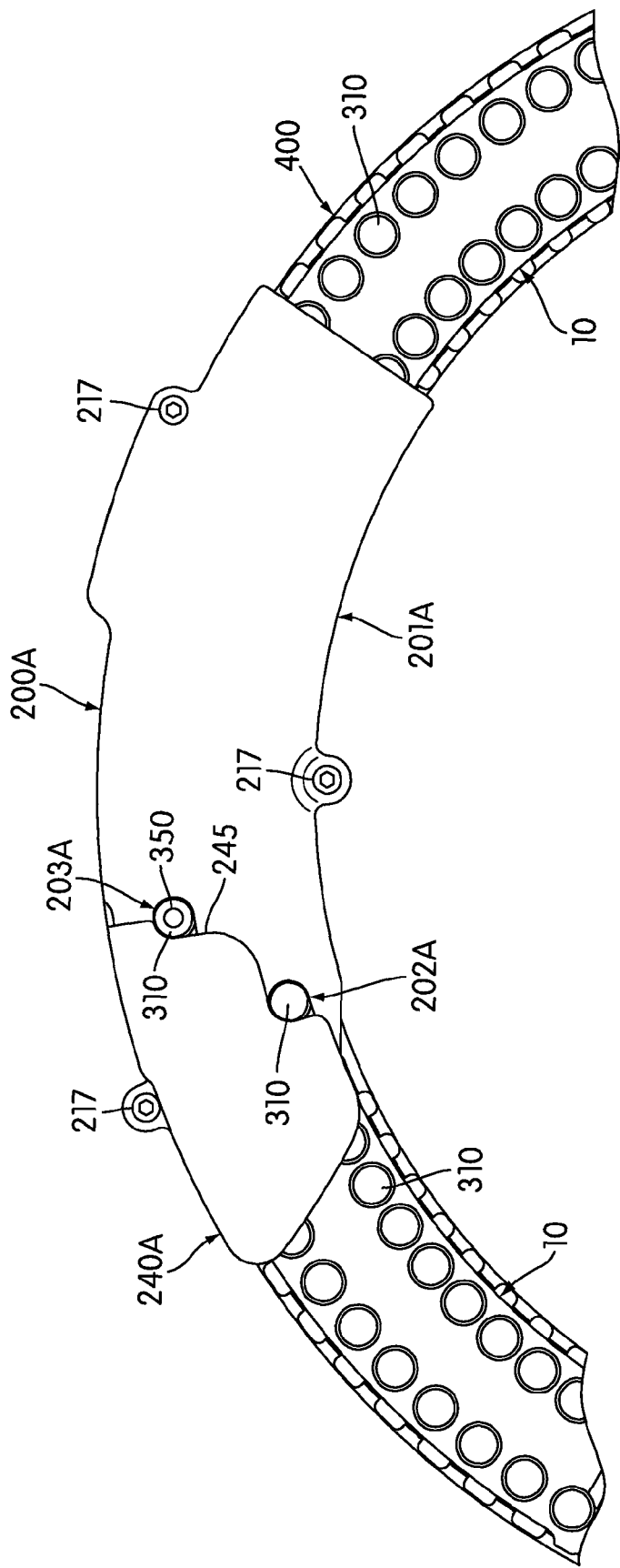
FIG. 7 is a partial top plan view showing a drip shield arranged above a sample transport carousel with a pipette tip extending through one of the access holes provided in the drip shield.

FIGS. 7-11 show a sequence which demonstrates how a drip shield embodying aspects of the invention permits a pipette tip extending out of a sample tube and through one of the access holes 202A or 203A can be conveyed laterally relative to the drip shield. As shown in FIG. 7, a pipette tip 350 is disposed within and extends through the outer access hole 203A of the drip shield 200A. The drip shield 200A shown in FIG. 7 is in a closed state, as the shutter 240A is in a position with respect to the cover plate 201A to define the access holes 202A and 203A. To convey the pipette tip laterally relative to the drip shield 200A, the transport carousel 400 is moved in a counterclockwise direction, as illustrated by arrow A in FIGS. 8-11.

Figure 8:
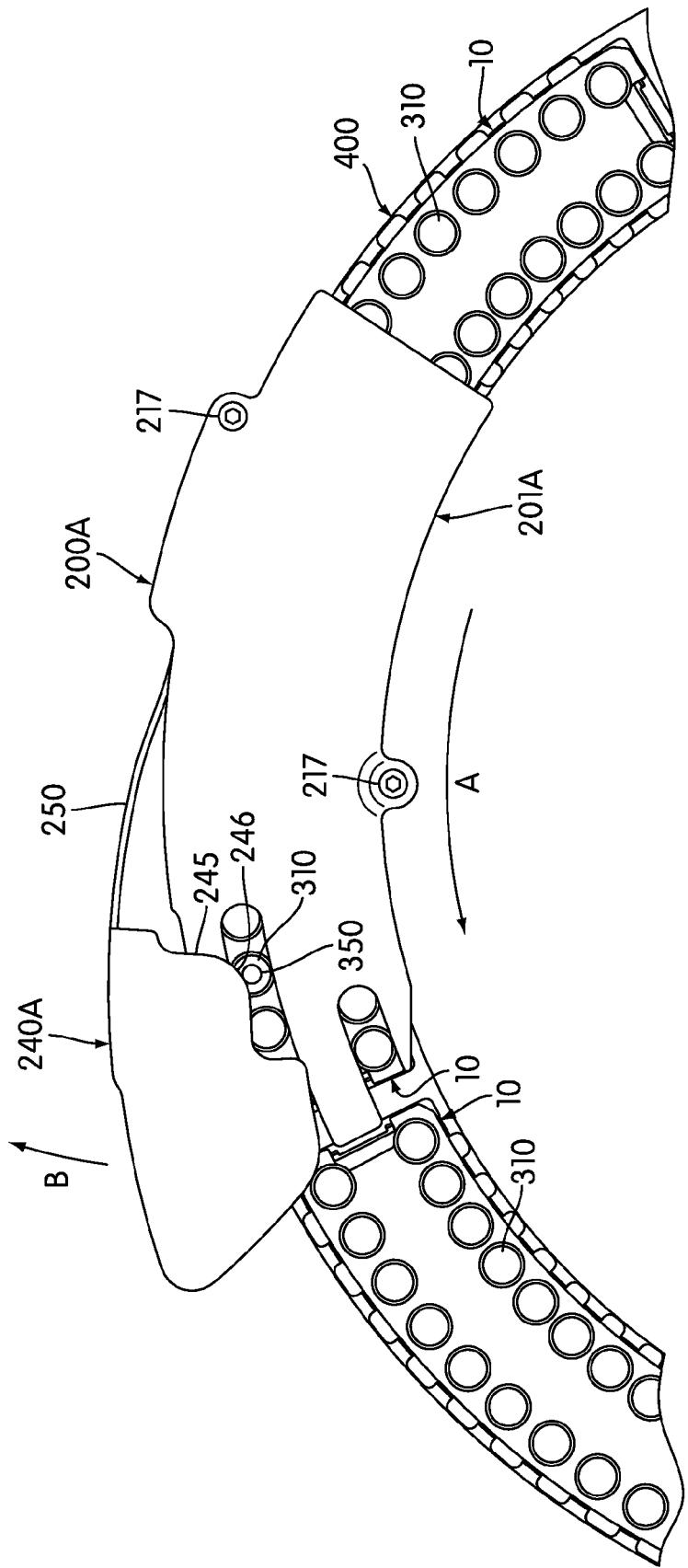
FIG. 8 is a partial top plan view of the drip shield arranged above the sample transport carousel with the shutter of the drip shield partially deflected with respect to the cover plate by engagement of the laterally moving pipette tip with an edge of the shutter.

As the transport carousel 400 continues to move in direction A, the pipette tip 350 engages the undulating edge 243 of the shutter 240A. Initially, the pipette tip 350 slides along the first straight portion 245, preferably having a slight forward inclination relative to the counterclockwise movement of the tip 350 so that the tip 350 does not get caught behind any back angled features of the edge of the shutter. The tip 350 then slides along the curved transition 246 of the shutter 240A as the carousel 400 continues to rotate. The lateral, counterclockwise movement of the pipette tip 350 and the engagement of the pipette tip 350 along the first straight portion 245 and curved transition 246 causes the shutter 240A to move laterally in the direction indicated by arrow B as the flexible arm 250 begins to flex outwardly, as shown in FIG. 8.

Figure 9:
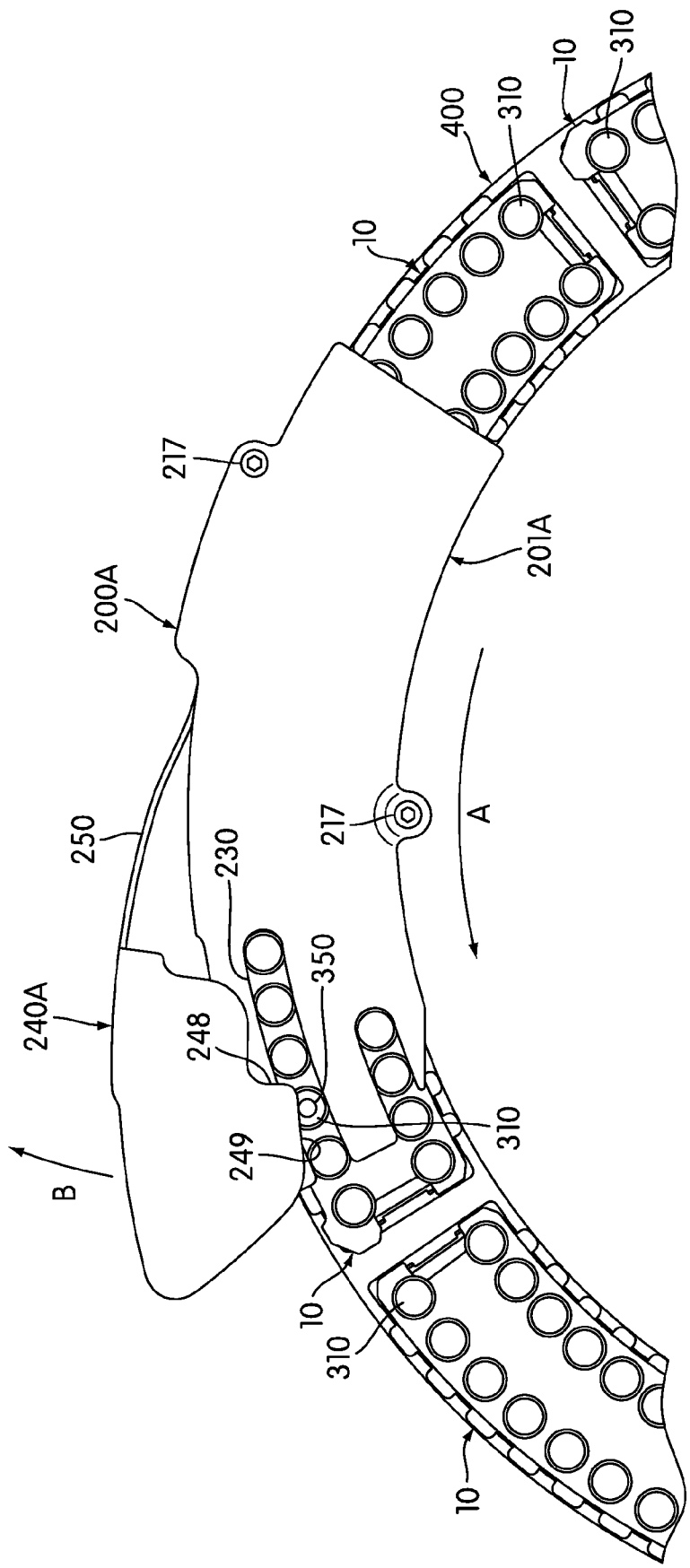
FIG. 9 is a partial top plan view of the drip shield arranged above the sample carousel with the shutter of the drip shield further deflected relative to the cover plate so as to permit the pipette tip extending out of a sample tube to be moved laterally away from the drip shield.

As shown in FIG. 9, continued counterclockwise movement of the sample carousel 400 in the direction A causes the pipette tip 350 to continue to slide along the undulating edge 243 of the shutter 240A past the second straight portion 248, which preferably has a slight forward inclination relative to the direction of movement of the pipette 350, and then along the inner edge 249. The continued movement of the pipette tip 350 along the undulating edge 243 of the shutter 240A during the lateral, counterclockwise movement of the pipette tip 350 causes the shutter 240A to further deflect laterally in the direction B, thereby permitting the pipette tip 350 to move laterally relative to the drip shield 200A within the outer slot 230 of the cover plate 201A. The drip shield 200A shown in FIG. 9 is in an open state, as the shutter 240A has now been moved with respect to the cover plate 201A so as to open the access holes 202A and 203A and permit the pipette tip 350 to be conveyed laterally with respect to the drip shield 200A.

Figure 10:
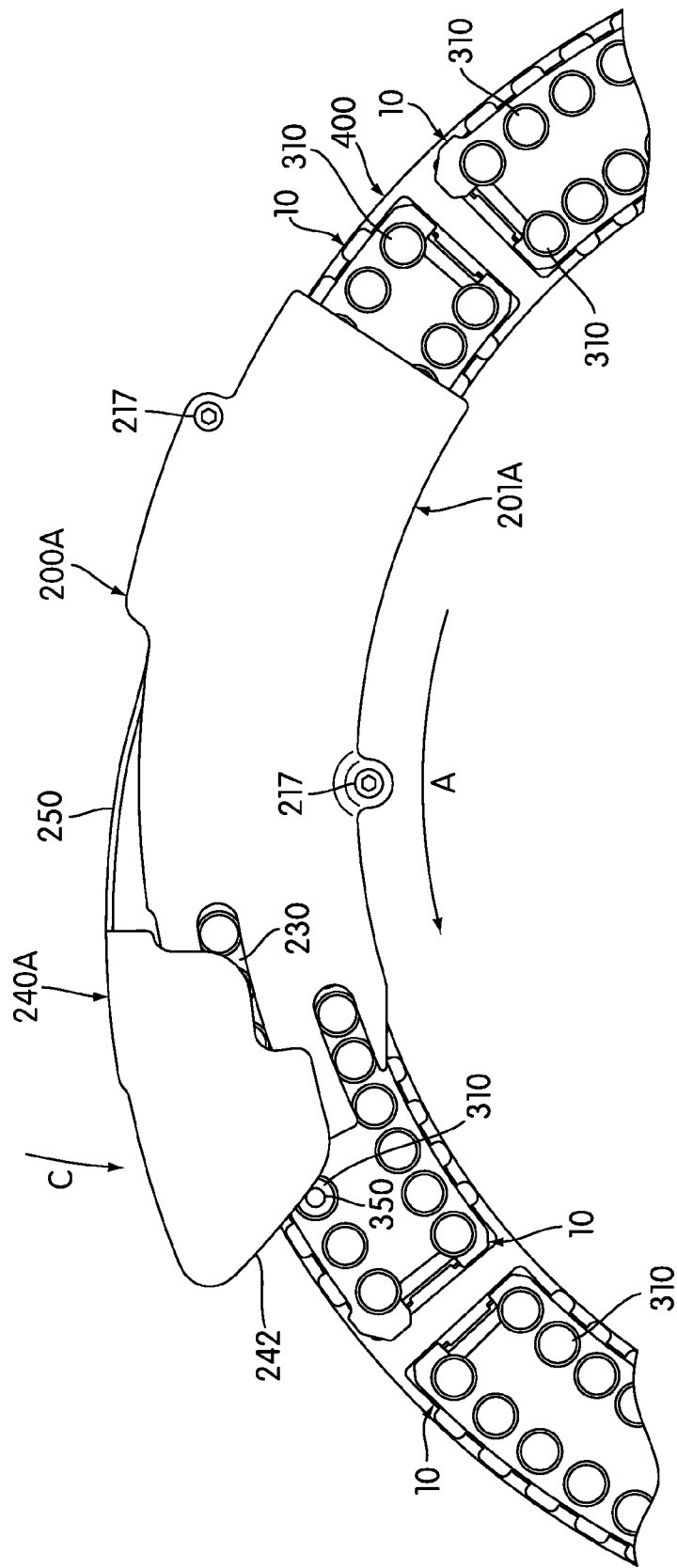
FIG. 10 is a partial top plan view of the drip shield arranged above the sample carousel with the shutter of the drip shield now moving back toward its undeflected position as the pipette tip continues to move laterally away from the drip shield.

As shown in FIG. 10, continued counterclockwise rotation of the transport carousel 400 in the direction A has now moved the pipette tip 350 beyond the outer slot 230 of the cover plate 201A. The shutter 240A, urged by the elasticity of the flexible arm 250, now begins to move in the direction indicated by arrow C back toward its undeflected position (i.e., toward the closed state). As the shutter 240A moves back toward its undeflected position, the pipette tip 350 slides along the edge 242 of the shutter 240A, which is preferably sloped as shown so that the pipette tip 350 remains in contact with the shutter for a longer period, allowing for a more gentle return of the shutter 240A to its undeflected position.

The estimated force required to deflect the shutter and permit the pipette tip to be moved laterally away from the drip shield is 1-2 pounds force. Ideally, the amount of force required to deflect the shutter is as low as possible, while still permitting smooth, consistent shutter return. As will be appreciated by persons of ordinary skill in the art, the deflection force of the shutter 240A of the embodiment shown in FIGS. 1-11 will depend on the material stiffness, the length of the arm 250, and the cross-section of the arm 250.

Figure 11:
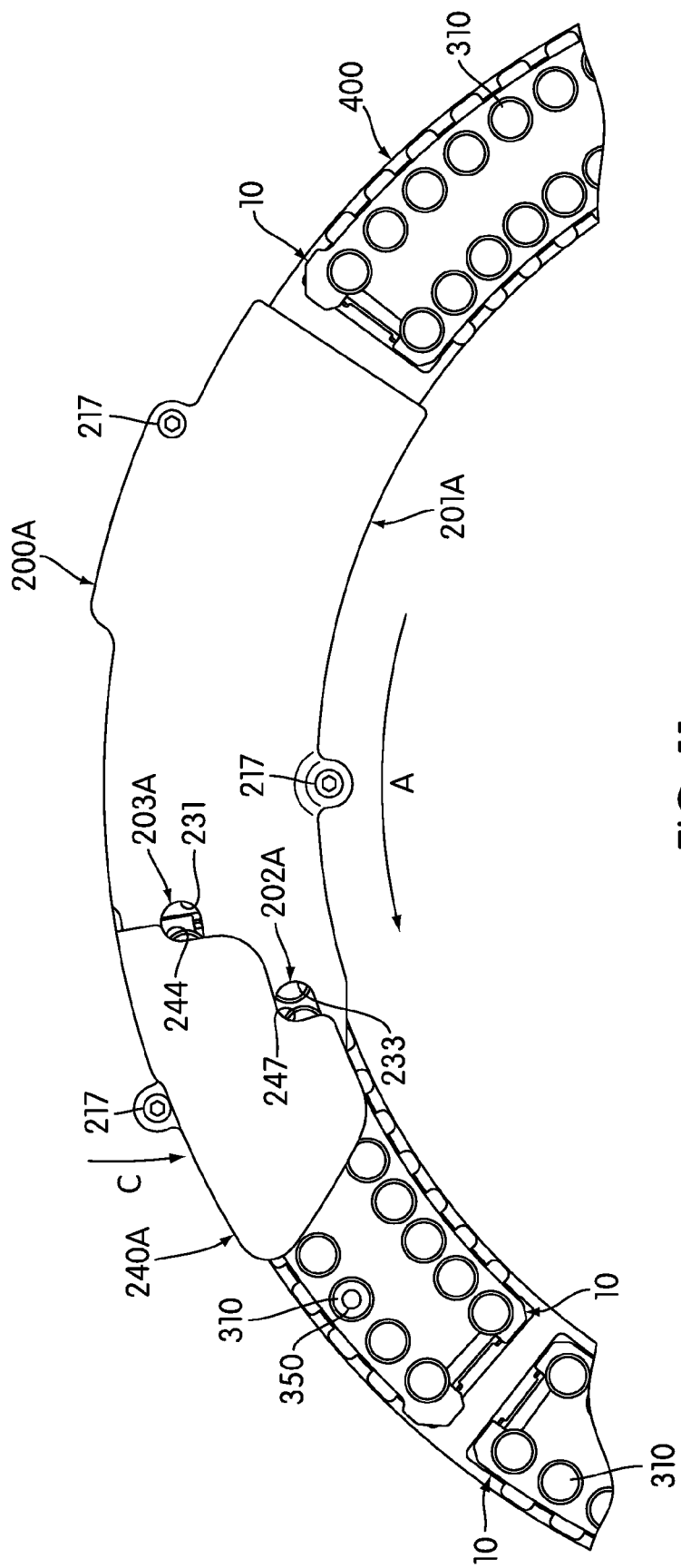
FIG. 11 is a partial top plan view of the drip shield arranged above the sample carousel with the pipette tip extending out of a sample tube now moved completely away from the drip shield and the shutter of the drip shield moved back to its undeflected position relative to the cover plate.

Finally, in FIG. 11 the tip 350 has moved completely away from the drip shield 200A, and the shutter 240A has now moved back to its undeflected position relative to the cover plate 201A. The sample carrier 10 can now be moved to a location where an operator can access and remove the dislodged pipette tip 350.

Figure 12:
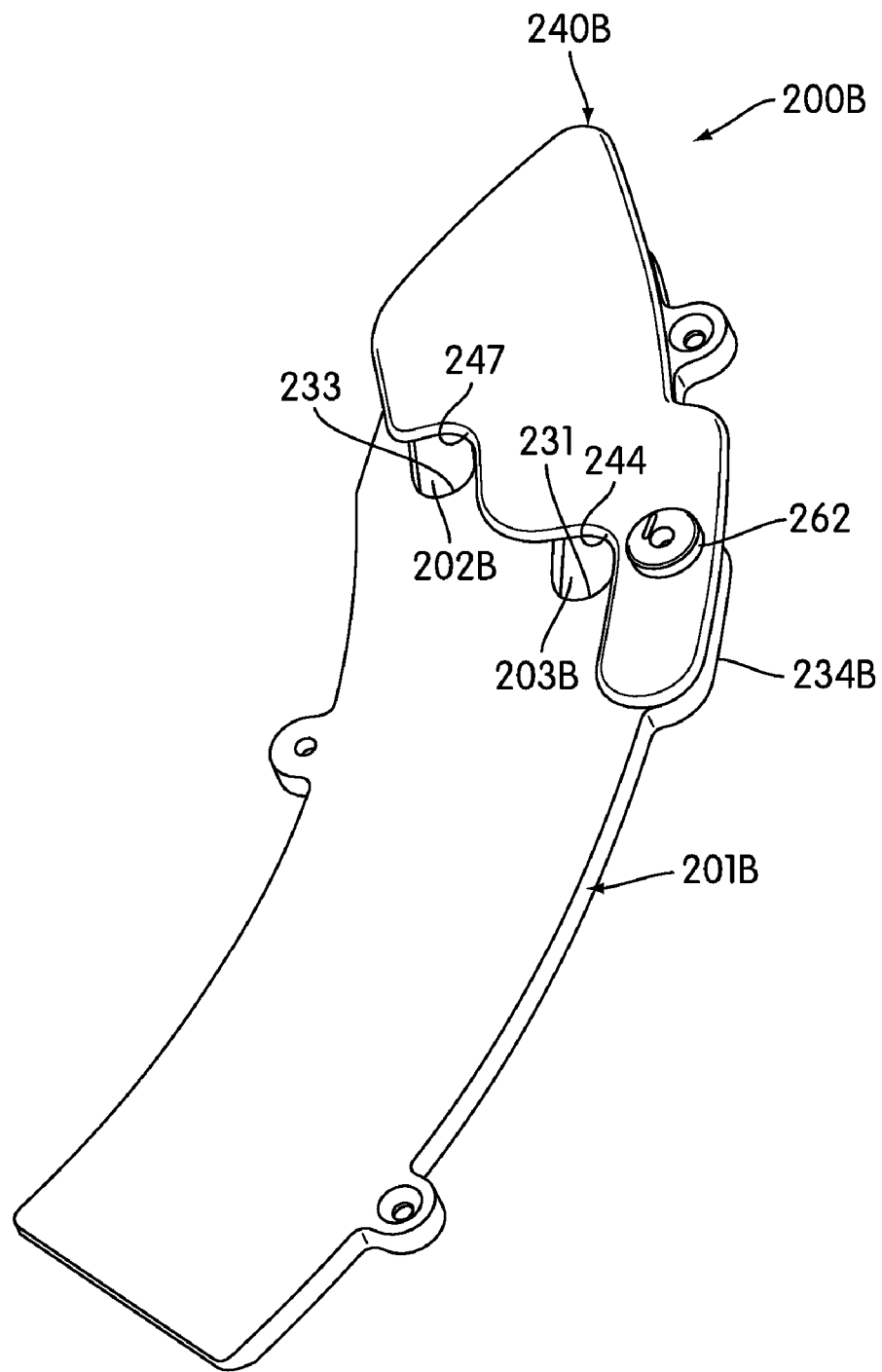
FIG. 12 is a top perspective view of a second embodiment of the drip shield of the invention.

A second embodiment of a drip shield according to the invention is indicated by reference number 200B in FIGS. 12-16. This drip shield 200B, shown in FIG. 12, is an assembly which includes a cover plate 201B and a shutter 240B which are dimensioned and cooperate to form a canopy over a sample carrier positioned thereunder.

Figure 13:
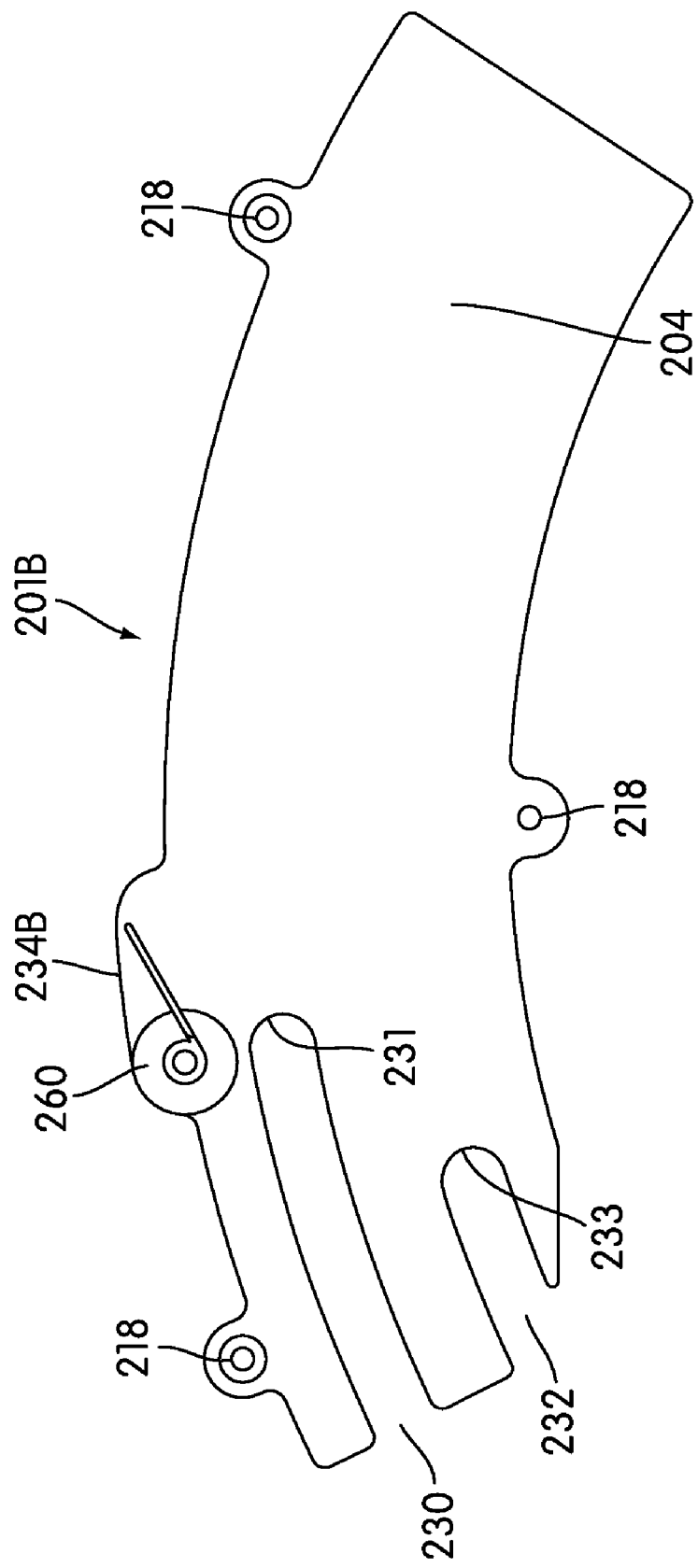
FIG. 13 is a top plan view of a cover plate of the second drip shield embodiment.

As shown in FIG. 13, cover plate 201B, like cover plate 201A, includes slot 230 with rounded closed end 231 and slot 232 with rounded closed end 233. Cover plate 201B further includes a shutter bracket 234B that is provided for attaching the shutter 240B thereto and projects outwardly from an edge of the cover plate 201B. A first spring element 260 is mounted on the shutter bracket 234B. Spring element 260 may comprise a torsional spring element, such as Stock No. TO-5085LS, available from Century Spring Corp. of Los Angeles, Calif.

Figure 14:
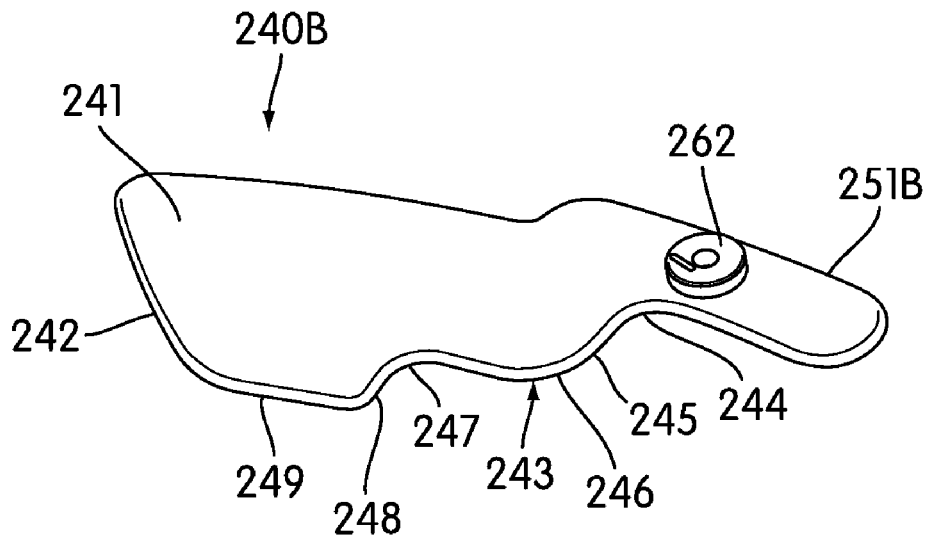
FIG. 14 is a top perspective view of a shutter of the second drip shield embodiment.
Figure 15:
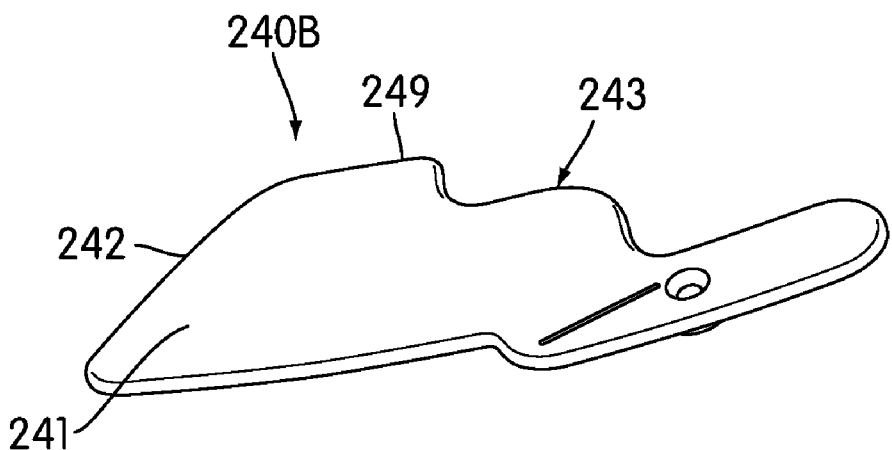
FIG. 15 is a bottom perspective view of the shutter of FIG. 14.
Figure 16:
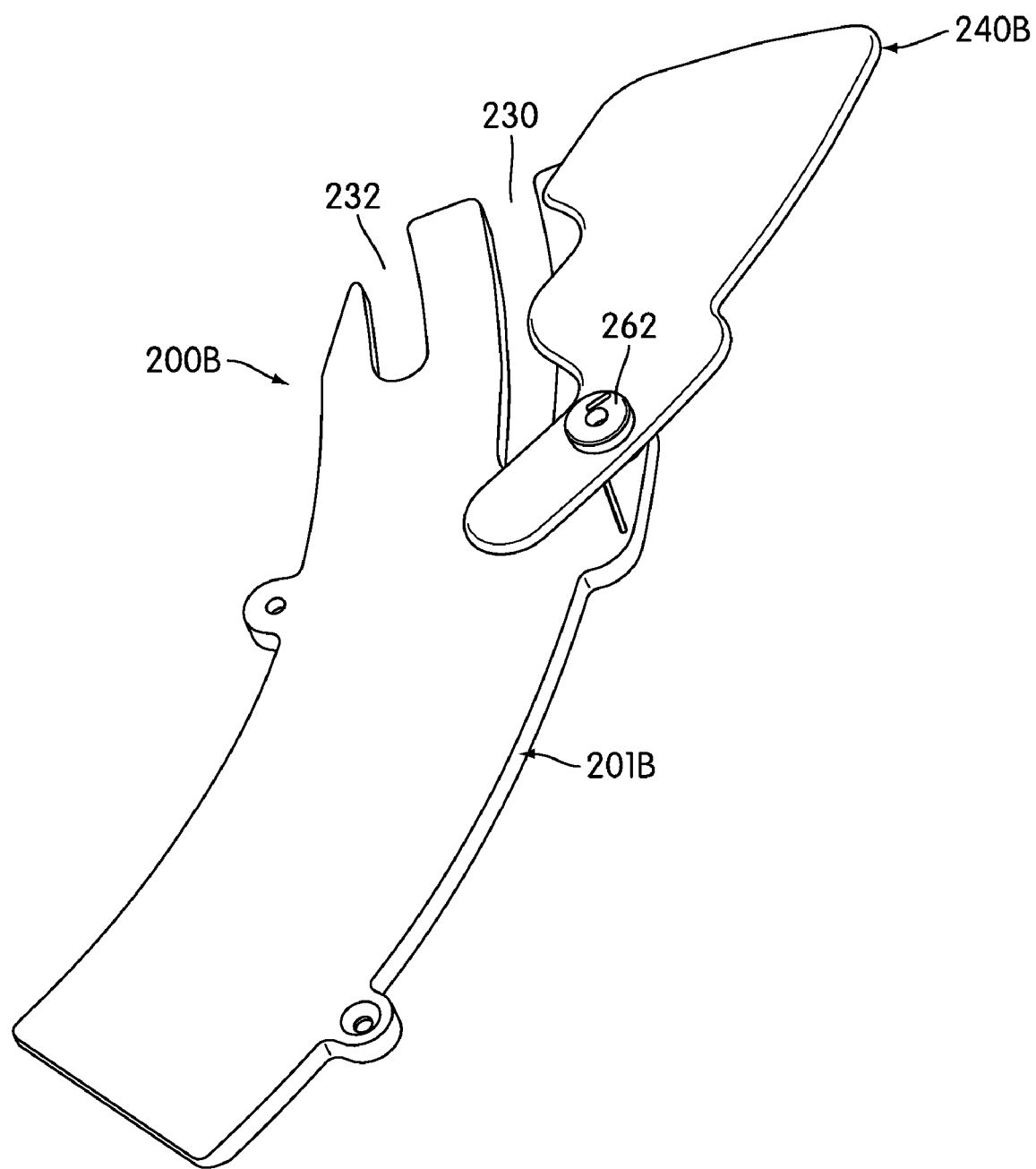
FIG. 16 is a top perspective view of the second drip shield embodiment with the shutter shown moved to a deflected position relative to the cover plate.

Referring to FIGS. 14 and 15, the shutter 240B includes a cover portion 241 and a mounting bracket 251B. The cover portion 241 includes a sloped end 242, a inner edge 249 and an undulating edge 243. Undulating edge 243 is generally defined by a first rounded fillet 244, a first straight portion 245, a curved transition 246, a second rounded fillet 247, and a second straight portion 248 which terminates at inner edge 249.

The mounting bracket 251B includes a spring element 262. The shutter 240B is installed onto the cover plate 201B so that the shutter 240B can pivot with respect to the cover plate 201B. The spring elements 260, 262 cooperate to bias the shutter 240B in the undeflected position (see FIG. 12) with respect to the cover plate 201B.

As best shown in FIG. 12, portions of the cover plate 201B and the shutter 240B cooperate to define the inner access hole 202B and outer access hole 203B. More specifically, the first fillet 244 of the shutter 240B and the rounded end 231 of the outer slot 230 form the perimeter of the outer access hole 203B. Similarly, the second fillet 247 of the shutter 240B and the rounded end 233 of the inner slot 232 cooperate to form the perimeter of the inner access hole 202B.

The drip shield 200B works in much the same way as the drip shield 200A described above. When a pipette tip (such as pipette tip 350 shown in FIGS. 2 and 7-11) is dislodged from a pipette tip mounting shaft of a robotic pipettor and extends through one of the access holes 202B or 203B of the drip shield 200B, the pipette tip can be conveyed laterally by means of a sample transport mechanism (e.g. sample carousel 400). The pipette tip engages the undulating edge 243 of the shutter 240B, thereby pivotally deflecting the shutter 240B against the force of the spring elements 260, 262 (see FIG. 16). Deflection of the shutter 240B permits the pipette tip 350 to be conveyed laterally out of slot 230 or 232 and away from the drip shield 200B. After the pipette tip 350 has been moved laterally away from the drip shield 200B, the spring elements 260, 262 bias the shutter 240B back to its undeflected position, as shown in FIG. 12.

Figure 17:
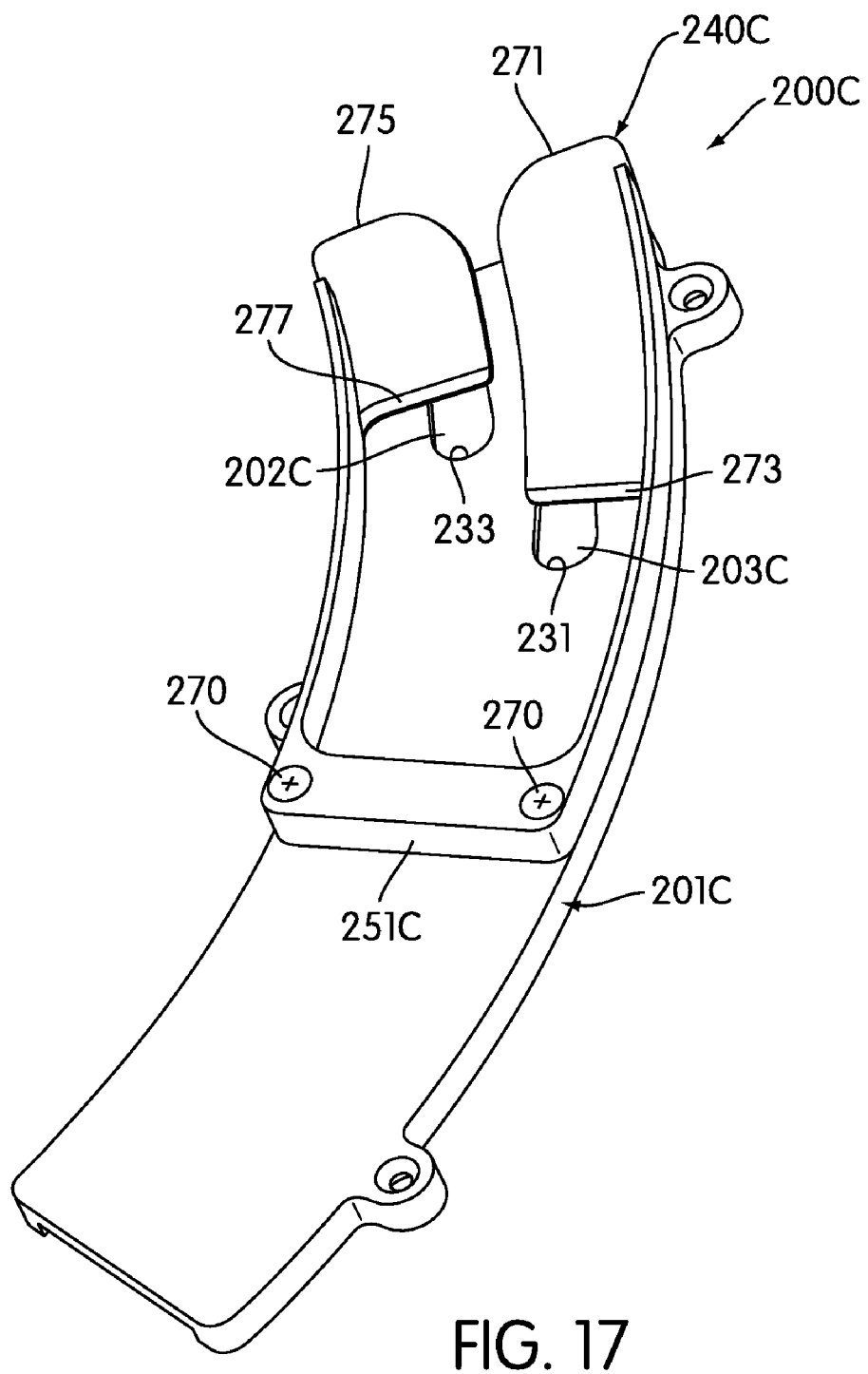
FIG. 17 is a top perspective view of a third embodiment of the drip shield of the invention.

A third embodiment of a drip shield according to the invention is indicated by reference number 200C in FIG. 17. The drip shield 200C shown in FIG. 17 is an assembly which includes a cover plate 201C and a shutter 240C which are dimensioned and cooperate to form a canopy over a sample carrier positioned thereunder.

Figure 18:
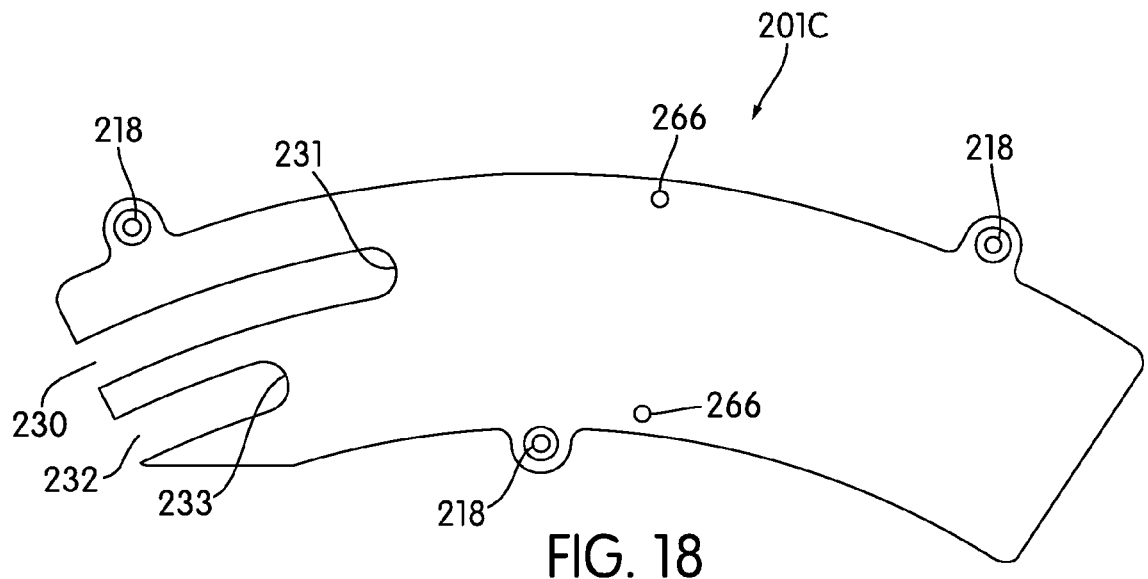
FIG. 18 is a top plan view of a cover plate of the third drip shield embodiment.

As shown in FIG. 18, cover plate 201C, like cover plates 201A and 201B, includes slot 230 with rounded closed end 231 and slot 232 with rounded closed end 233. Cover plate 201C further includes mounting holes 266 for attaching the shutter 240C to the cover plate 201C as described below.

Figure 19:
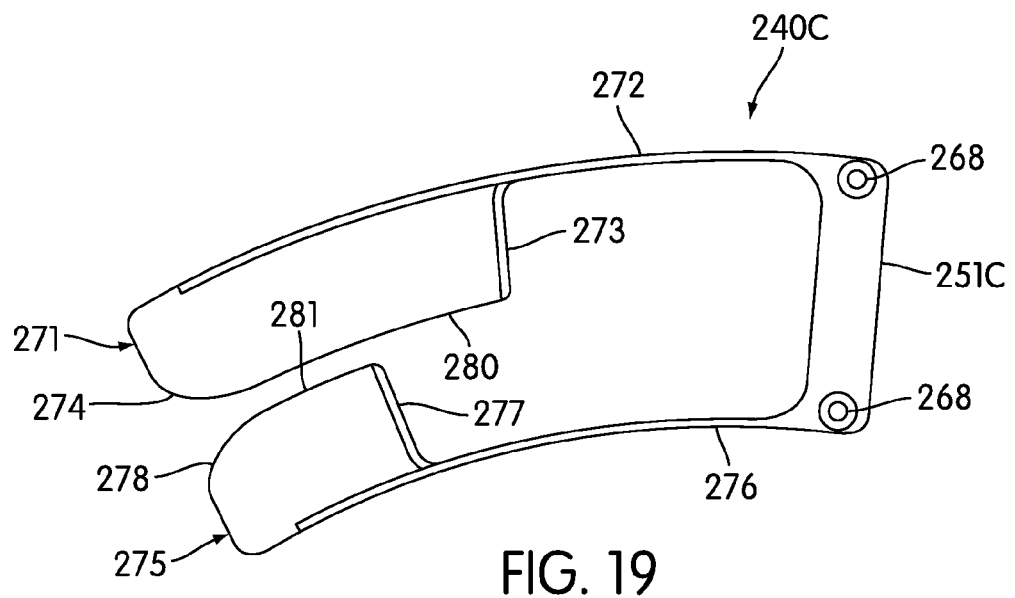
FIG. 19 is a top plan view of a shutter of the third drip shield embodiment.

Referring to FIG. 19, the shutter 240C includes two cover portions 271, 275, each with a flexible arm 272, 276, respectively, and a mounting bracket 251C connecting the two cover portions. Cover portion 271 includes a sloped end 274, a inner edge 280 and an actuating edge 273. Similarly, cover portion 275 includes a sloped end 278, a inner edge 281 and an actuating edge 277.

The mounting bracket 251C includes fastener holes 268. Shutter 240C is installed onto the cover plate 201C by means of suitable mechanical fasteners (such as screws 270) inserted through fastener holes 268 into mating holes 266 (which may be threaded) formed in cover plate 201C.

As best shown in FIG. 17, portions of the cover plate 201C and the shutter 240C cooperate to define the inner access hole 202C and outer access hole 203C. More specifically, the actuating edge 273 of cover portion 271 and the rounded end 231 of the outer slot 230 form the perimeter of the outer access hole 203C. Similarly, the actuating edge 277 of the cover portion 275 and the rounded end 233 of the inner slot 232 cooperate to form the perimeter of the inner access hole 202C. Note that cover portion 275 is shorter than cover portion 271, just as inner slot 232 is shorter than outer slot 230.

When a pipette tip (such as pipette tip 350 shown in FIGS. 7-11) is dislodged from a pipette tip mounting shaft and extends through one of the access holes 202C or 203C of the drip shield 200C, the pipette tip may bemoved laterally by means of a sample transport mechanism (e.g. sample carousel 400). The pipette tip engages the actuating edge 273 or 277 of the shutter 240C, thereby deflecting the corresponding cover portion 271 or 275 against the resilience of the corresponding flexible arm 272 or 276. With a cover portion 271 or 275 of the shutter 240C deflected, the pipette tip can be moved laterally out of the slot 230 or 232 and away from the drip shield 200C, the pipette tip sliding along edge 280 or 281 as it continues to move laterally relative to the drip shield 200C. After the pipette tip has been moved laterally away from the drip shield 200C, the flexible arm 272 or 276 biases the corresponding cover portion 271 or 275 back to its undeflected position, as shown in FIG. 17. The rounded end 274 or 278 of the cover portion 271 or 275 permits a gentle return of the cover portion 274 or 275 to its undeflected position as the pipette tip disengages from the cover portion.

Still further alternative drip shield configurations include flexible rubber or foam flaps (as opposed to a rigid shutter) disposed over slots formed in the cover plate. The flaps cover all but a portion of the slots so as to define access holes permitting access to sample tubes beneath the drip shield, but flex out of the way of a pipette tip being conveyed laterally through the slot.

An apparatus incorporating a drip shield according to the present invention may include sensors and automated control (e.g., a programmed microprocessor) to provide automated warnings and appropriate sample carrier movement when a pipette tip is dislodged from an automated sampler device and is left in the sample tube, extending through the drip shield. As described in, e.g., Ammann et al., U.S. Pat. No. 6,335,166, under normal sampling procedures, a disposable pipette tip is placed onto the end of a pipette tip mounting shaft of a robotic pipetting device prior to transferring sample from a particular sample tube 300. When sample transfer from that sample tube is complete, the disposable pipette tip is discarded, typically into a waste container. In the apparatus shown in FIG. 1, the robotic pipetting device moves the transfer pipette tip into a pipette tip chute 500, moving the disposable pipette tip through a slot 501 formed in the side of the chute 500, where the disposable pipette tip is stripped off the robotic pipetting device and directed into a waste container (not shown) by the pipette tip chute 500. As sensor is provided (e.g., an optical sensor, not shown) to confirm that a pipette tip is in fact on the pipette tip mounting shaft prior to the stripping procedure.

Figure 20:
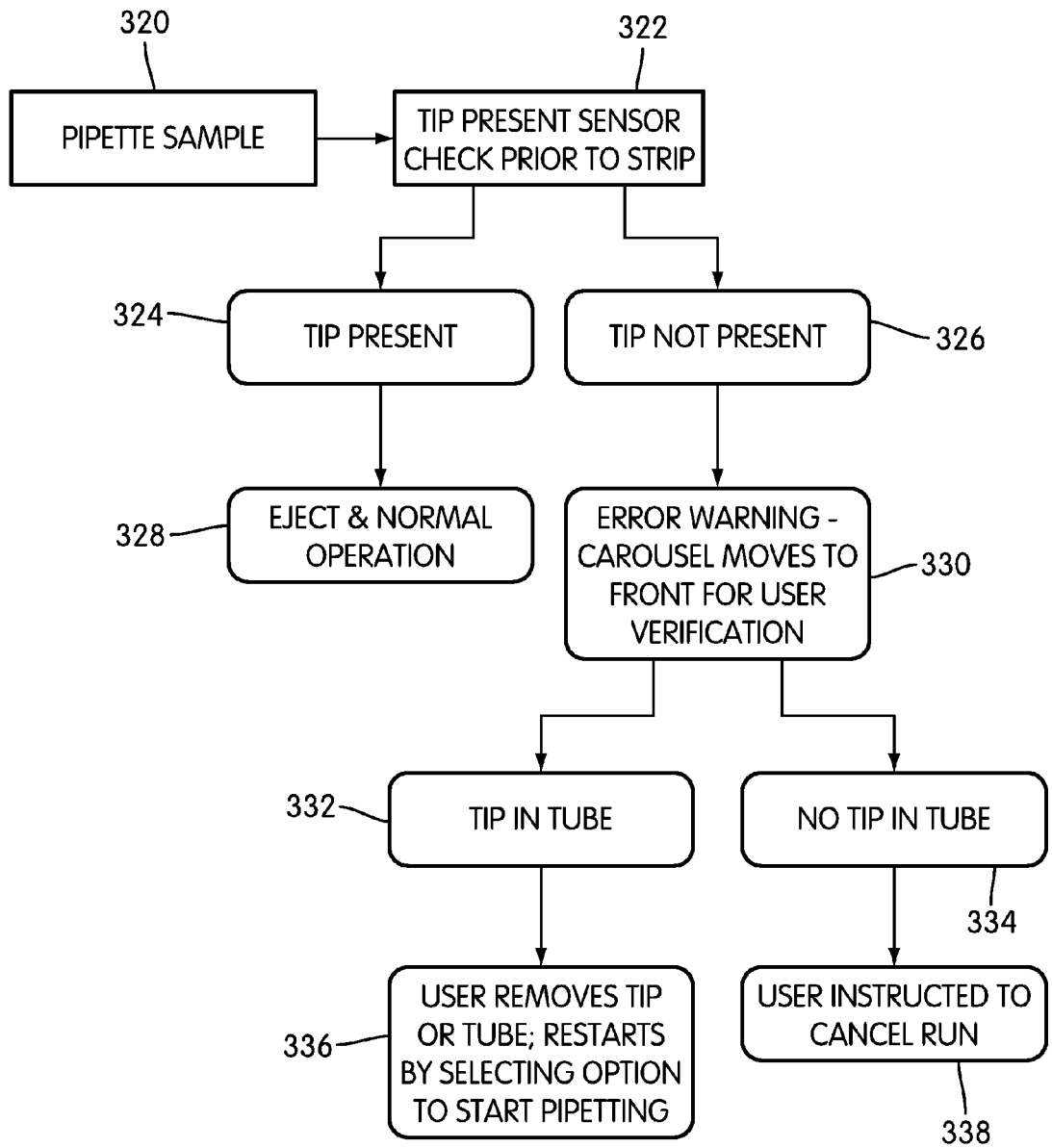
FIG. 20 is a flow chart showing a procedure to be followed when a pipette tip has been left in a sample tube.

The procedure for determining if a dislodged pipette tip extends through the drip shield is illustrated in the flow chart of FIG. 20. Step 320 represents the automated sampling procedure whereby sample is transferred from a sample tube. The sample tube may be provided with a penetrable cap having one or more frangible seals and, optionally, a filter means (e.g., as described in Kacian, et al., U.S. Patent No. 6,893,612), and the automated sampling procedure 320 may include piercing the seal(s) and filter means of the penetrable cap with the pipette tip to access the contents of the sample tube. In step 322, the pipetting device is moved to an operative position with respect to a tip sensor to determine if the disposable pipette tip is still secured on the pipette tip mounting shaft. If the pipette tip is present (step 324), the pipette tip is ejected and normal operation continues (step 328). If the pipette tip is not present (step 326), an error warning (e.g., an alarm and/or a visual warning, such as a light or a warning icon on a graphical user interface) is provided, and the sample transport (e.g., carousel 400) moves the sample tube away from the drip shield to a place where the sample tube can be accessed by the operator to determine if a pipette tip is stuck in the sample tube (step 330). If there is no pipette tip in the sample tube (step 334) the operator is instructed to terminate the run (step 338). If a pipette tip is stuck in a sample tube (step 332), the operator removes the pipette tip and restarts the apparatus to continue operation (step 336).

All disclosures referred to herein are hereby incorporated by reference in their entireties. No disclosure referred to herein is admitted to be prior art to the claimed invention.

While the present invention has been described and shown in considerable detail with disclosure to certain preferred embodiments, those skilled in the art will readily appreciate other embodiments of the present invention. Accordingly, the present invention is deemed to include all modifications and variations encompassed within the spirit and scope of the following appended claims.

The invention claimed is:

1. An apparatus for preventing unwanted materials from being deposited into receptacles carried by an automated conveyor, the apparatus comprising:
   a first cover member including one or more slots, each slot extending from an end portion of the first cover member; and
   a second cover member attached to the first cover member and configured to be moveable with respect to the first cover member between a closed state and an open state, such that
      in the closed state, the second cover member is operatively positioned with respect to the first cover member so that the second cover member covers all but a portion of each slot, the uncovered portion of each slot defining an access hole for receiving a pipette tip therethrough to access receptacles positioned beneath the apparatus; and
      in the open state, the second cover member is operatively positioned with respect to the first cover member so that at least one of the slots is substantially uncovered, thereby permitting a pipette tip extending through the portion of the slot defining the corresponding access hole to be laterally conveyed relative to the first cover member and out of the slot.

2. The apparatus of claim 1, wherein each access hole is generally round when the second cover member is in the closed state.

3. The apparatus of claim 1, wherein the first cover member includes two slots.

4. The apparatus of claim 3, wherein the slots are of unequal length.

5. The apparatus of claim 1, wherein the second cover member includes an edge configured to cause the second cover member to move from the closed state to the open state as a pipette tip extending through one of the access holes is laterally conveyed and engages the edge.

6. The apparatus of claim 5, wherein the edge has an undulating shape.

7. The apparatus of claim 5, further comprising a bias element adapted to bias the second cover member toward the closed state.

8. The apparatus of claim 7, wherein the bias element comprises a flexible arm or a torsional spring mechanism.

9. The apparatus of claim 1, wherein the first and second cover members cooperate to define a canopy positioned over a portion of an automated conveyor, the canopy having a shape generally conforming to the shape of the portion of the automated conveyor when the second cover member is in the closed state.

10. The apparatus of claim 9, wherein the canopy has an arcuate shape conforming to a generally circular automated conveyor.

11. The apparatus of claim 10, wherein, when the second cover member is in the closed state, the first and second cover members cooperate to define an outer access hole operatively positioned with respect to an outer ring of receptacles carried on the circular automated conveyor and an inner access hole operatively positioned with respect to an inner ring of receptacles carried on the circular automated conveyor, the inner ring being disposed radially inwardly from the outer ring.

12. The apparatus of claim 11, wherein the outer access hole and the inner access hole are angularly offset from one another.

13. The apparatus of claim 1, wherein the second cover member comprises:
   a cover portion;
   a flexible arm extending from the cover portion; and
   a mounting bracket at an end of the flexible arm opposite the cover portion, wherein the second cover member is secured to the first cover member at the mounting bracket and the flexible arm is constructed and arranged to permit the cover portion to move relative to the first cover member between the closed state and the open state and to bias the cover portion toward the closed state.

14. The apparatus of claim 13, wherein the cover portion includes an undulating edge, wherein one or more portions of the undulating edge define a portion of each of the access holes, and wherein the undulating edge is configured so that lateral movement of a pipette tip extending out of one of the access holes causes the pipette tip to engage the undulating edge, thereby causing the cover portion to move from the closed state to the open state.

15. The apparatus of claim 14, wherein the cover portion further includes a sloped end configured to be engaged by the pipette tip as the pipette tip is conveyed laterally away from one of the access holes, and wherein the second cover member is urged by the flexible arm back toward the closed position as the pipette tip engages the sloped end.

16. The apparatus of claim 1, wherein the second cover member comprises:
a mounting bracket at which the second cover member is secured to the first cover member;
a first cover portion;
a first flexible arm extending from the first cover portion and connected at an end thereof to a first end of the mounting bracket, wherein the first flexible arm is constructed and arranged to permit the first cover portion to move relative to the first cover member between the closed state and the open state and to bias the first cover portion toward the closed state, wherein the first cover portion and the first cover member cooperate to define a first access hole when the first cover portion is in the closed state;
a second cover portion; and
a second flexible arm extending from the second cover portion and connected at an end thereof to a second end of the mounting bracket, wherein the second flexible arm is constructed and arranged to permit the second cover portion to move relative to the first cover member between the closed state and the open state and to bias the second cover portion toward the closed state, wherein the second cover portion and the first cover member cooperate to define a second access hole when the second cover portion is in the closed state.

17. The apparatus of claim 1, wherein the second cover member comprises:
a cover portion;
a mounting bracket extending from the cover portion, wherein the second cover member is pivotally connected to the first cover member at the mounting bracket to permit the cover portion to pivot relative to the first cover member between the closed state and the open state; and
a torsional spring mechanism constructed and arranged to bias the cover portion toward the closed state.

18. The apparatus of claim 17, wherein the cover portion includes an undulating edge, wherein one or more portions of the undulating edge define a portion of each of the access holes, and wherein the undulating edge is configured so that lateral movement of a pipette tip extending out of one of the access holes causes the pipette tip to engage the undulating edge, thereby causing the cover portion to pivot from the closed state to the open state.

19. The apparatus of claim 18, wherein the cover portion further includes a sloped end configured to be engaged by the pipette tip as the pipette tip is conveyed laterally away from one of the access holes, and wherein the second cover member is urged by the torsional spring mechanism back toward the closed position as the pipette tip engages the sloped end.

20. The apparatus of claim 1, wherein the first and second cover members are made from plastic.

21. The apparatus of claim 1, further comprising mounting posts for mounting the apparatus to a stationary surface and holding the apparatus in a fixed relationship over the receptacles carried on the automated conveyor.

22. The apparatus of claim 1, wherein the first cover member includes two or more raised runners extending along a bottom surface thereof in a direction corresponding to the direction of movement of receptacles relative to the apparatus, each pair of adjacent runners defining a channel therebetween.

23. The apparatus of claim 22, wherein the runners have tapered ends.

24. A system for transferring substance to or from each of a plurality of receptacles comprising:
(A) a substance transfer mechanism for use in conjunction with a pipette tip and adapted to insert a pipette tip removably engaged by the substance transfer mechanism into a receptacle to transfer substance to or from the receptacle;
(B) a transport mechanism for moving a plurality of receptacles in generally upright orientations into an operative location with respect to the substance transfer mechanism, where the substance transfer mechanism can access each receptacle to insert a pipette tip into the receptacle; and
(C) a drip shield disposed over a portion of the transport mechanism at the operative location for preventing unwanted materials from being deposited into receptacles carried by the transport mechanism, the drip shield comprising:
(1) a first cover member including one or more slots, each slot extending from an end portion of the first cover member; and
(2) a second cover member attached to the first cover member and configured to be moveable with respect to the first cover member between a closed state and an open state, such that
(a) in the closed state, the second cover member is operatively positioned with respect to the first cover member so that the second cover member covers all but a portion of each slot, the uncovered portion of each slot defining an access hole for receiving a pipette tip therethrough to access a receptacle positioned beneath the drip shield; and
(b) in the open state, the second cover member is operatively positioned with respect to the first cover member so that at least one of the slots is substantially uncovered, thereby permitting a pipette tip extending through the portion of the slot defining the corresponding access hole to be laterally conveyed by the transport mechanism relative to the first cover member and out of the slot.

25. The system of claim 24, wherein the substance transfer mechanism comprises a robotic pipetting device.

26. The system of claim 24, wherein the transport mechanism comprises:
a sample carrier constructed and arranged to hold a plurality of receptacles in generally upright orientations; and
a sample carrier conveyor constructed and arranged to convey multiple sample carriers and to sequentially position each sample carrier with respect to the substance transfer mechanism so that at least one of the receptacles carried by the sample carrier is in the operative location.

27. The system of claim 26, wherein the sample carrier conveyor comprises a carousel which conveys sample carriers by rotating.

28. A method for transferring substance to or from a receptacle and for preventing unwanted materials from being deposited into the receptacle comprising:
(A) providing the apparatus of claim 1 at a substance transfer location;
(B) transporting a receptacle to the substance transfer location;
(C) accessing the receptacle through one of the access holes with a pipette tip engaged by a substance transfer mechanism;

(D) transferring substance into or out of the pipette tip accessing the receptacle through the access hole; and (E) after the transferring step, determining if the pipette tip is still engaged by the substance transfer mechanism, and if the pipette tip is no longer engaged by the substance transfer mechanism, conveying the receptacle laterally with respect to the apparatus, and, if the pipette tip no longer engaged by the substance transfer mechanism is extending through the access hole, causing the second cover member to move from the closed state to the open state to permit the pipette tip extending through the access hole to be laterally conveyed relative to the apparatus and away from the location of the access hole.

29. The method of claim 28, wherein accessing the receptacle includes piercing a closure device coupled to the receptacle.

30. The method of claim 28, wherein the receptacle is a tubular container.

31. The method of claim 28, wherein the receptacle contains a specimen retrieval device.

* * * * *

UNITED STATES PATENT AND TRADEMARK OFFICE
CERTIFICATE OF CORRECTION

| | | |
|---|---|---|
| PATENT NO. | : 7,763,467 B2 | Page 1 of 1 |
| APPLICATION NO. | : 11/673903 | |
| DATED | : July 27, 2010 | |
| INVENTOR(S) | : Knight | |

It is certified that error appears in the above-identified patent and that said Letters Patent is hereby corrected as shown below:

Claim 16:
      Col. 15, line 23, change "armis" to --arm is--.

Signed and Sealed this

Sixteenth Day of November, 2010

David J. Kappos
*Director of the United States Patent and Trademark Office*